United States Patent
Kim et al.

(10) Patent No.: US 11,518,817 B2
(45) Date of Patent: *Dec. 6, 2022

(54) MONOCLONAL ANTIBODY SPECIFICALLY BINDING TO MRS

(71) Applicant: ONCOTAG DIAGNOSTICS CO., LTD., Suwon (KR)

(72) Inventors: Sunghoon Kim, Seoul (KR); Nam Hoon Kwon, Gyeonggi-do (KR)

(73) Assignee: ONCOTAG DIAGNOSTICS CO., LTD., Suwon (KR)

( * ) Notice: Subject to any disclaimer, the term of this patent is extended or adjusted under 35 U.S.C. 154(b) by 230 days.

This patent is subject to a terminal disclaimer.

(21) Appl. No.: 16/612,174

(22) PCT Filed: May 11, 2018

(86) PCT No.: PCT/KR2018/005442
§ 371 (c)(1),
(2) Date: Nov. 8, 2019

(87) PCT Pub. No.: WO2018/208121
PCT Pub. Date: Nov. 15, 2018

(65) Prior Publication Data
US 2021/0130491 A1 May 6, 2021

(30) Foreign Application Priority Data
May 11, 2017 (KR) .................. 10-2017-0058896

(51) Int. Cl.
*C07K 16/40* (2006.01)
*G01N 33/574* (2006.01)

(52) U.S. Cl.
CPC ....... *C07K 16/40* (2013.01); *G01N 33/57496* (2013.01); *C07K 2317/10* (2013.01); *C07K 2317/33* (2013.01); *C07K 2317/92* (2013.01); *G01N 2333/9015* (2013.01)

(58) Field of Classification Search
None
See application file for complete search history.

(56) References Cited

U.S. PATENT DOCUMENTS

| 8,981,045 B2 * | 3/2015 | Greene .................. G01N 33/68 530/300 |
| 2007/0292921 A1 | 12/2007 | Hayes et al. |
| 2015/0361412 A1 | 12/2015 | Greene et al. |

FOREIGN PATENT DOCUMENTS

| WO | 2011140135 A2 | 11/2011 |
| WO | 2011150279 A2 | 12/2011 |

OTHER PUBLICATIONS

Feb. 18, 2019 (WO) ISR PCT Application No. PCT/KR2018/005442.
PDB: 4KUZ_L: Chain L, Crystal Structure Of Anti-emmprin Antibody 4a5 Fab In Trigonal Form, Aug. 15, 2014.
GenBank: AAA88262.1: immunoglobulin mu chain, partial [Mus musculus]. Jul. 26, 2016.
Kwon et al. "Dual role of methionyl-tRNA synthetase in the regulation of translation and tumor suppressor activity of aminoacyltRNA synthetase-interacting multifunctional protein-3" PNAS, Dec. 6, 2011, vol. 108, No. 49. 19635-19640.
PDB: 4KUZ: Teplyakov et al. Crystal Structure Of Anti-emmprin Antibody 4a5 Fab In Trigonal Form, deposited on May 22, 2013.
Kehry et al. "Amino acid sequence of a mouse immunoglobulin m chain" Proc. Natl. Acad. Sci. USA, vol. 76, No. 6, pp. 2932-2936, Jun. 1979.

* cited by examiner

*Primary Examiner* — Sharon X Wen
(74) *Attorney, Agent, or Firm* — Banner & Witcoff, Ltd.

(57) ABSTRACT

The present invention relates to an anti-MRS monoclonal antibody and, more specifically, to an antibody or a fragment thereof characterized by specifically binding to a fragment represented by amino acid 861-900 of a human-derived methionyl-tRNA synthetase (MRS) protein set forth in SEQ ID NO:1, a method for producing the same, and a composition for diagnosing cancer comprising the same. The antibody or the fragment thereof of the present invention specifically binds to the human-derived MRS, and has no cross-reactivity with other proteins comprising the same ARS family. Therefore, as MRS detection is possible, the antibody or a fragment thereof can be effectively used for diagnosing MRS-related cancer.

4 Claims, 10 Drawing Sheets
(5 of 10 Drawing Sheet(s) Filed in Color)
Specification includes a Sequence Listing.

MONOCLONAL ANTIBODY SPECIFICALLY BINDING TO MRS

RELATED APPLICATION DATA

This application is a National Stage Application under 35 U.S.C. 371 of co-pending PCT application number PCT/KR2018/005442 designating the United States and filed May 11, 2018; which claims the benefit of KR application number 10-2017-0058896 and filed May 11, 2017 each of which are hereby incorporated by reference in their entireties.

SEQUENCE LISTING

The instant application contains a Sequence Listing which has been filed electronically in ASCII format and is hereby incorporated by reference in its entirety. Said ASCII copy, created on Dec. 4, 2019, is named 009041_00003_US_SL.txt and is 65,749 bytes in size.

TECHNICAL FIELD

The present application claims priority from Korean Patent Application No.10-2017-0058896, filed on May 11, 2017, the entire contents of which are incorporated herein by reference.

The present invention relates to a monoclonal antibody which binds specifically to MRS, more specifically to an antibody or a fragment thereof which specifically binds to a peptide fragment defined by the $861^{st}$ to $900^{th}$ amino acid residues of a human-derived methionyl-tRNA synthetase (MRS) protein as set forth in SEQ ID NO: 1, a method for the preparation of the same and a composition for diagnosis of cancer comprising the same.

BACKGROUND OF THE INVENTION

Aminoacyl-tRNA synthetase (ARS) is an enzyme that attaches a specific amino acid to its corresponding tRNA. In the case of higher organisms, it consists of 23 kinds of enzymes including three types involved in the formation of multisynthetase complexes such as AIMP1 (p43), (AIMP2) p38, and (AIMP3) p18 in addition to 20 enzymes according to different types of amino acids. Besides those constituting the multisynthetase complex, some exist as a free form. Recently, however, some of these enzymes have been reported to have various different active functions in a specific environment in addition to the basic function, and MRS (methionyl-tRNA synthetase) is one of them. MRS is an essential enzyme that binds methionine to the initiator and elongator $tRNA^{Met}$ for translation. Because Met-tRNA$^{Met}$ is required for the initiation of protein polymerization reaction and extension of polypeptides, it is in a critical position to regulate not only translation but also potentially other biological processes. For example, MRS regulates specificity for tRNA in response to oxidative stress and allows more methionine to be inserted into the polypeptide chain being synthesized, thereby eliminating reactive oxygen species by the increased methionine (Lee et al., 2014; Wiltrout et al., 2012). Recently MRS has also been found to be involved in a variety of diseases. Upon UV irradiation, the enzymatic activity of MRS is suppressed as the S662 position is phosphorylated in a GCN2-dependent manner and the initiation response of translation is inhibited (Kang et al., 2012; Kwon et al., 2011). When MRS is phosphorylated, it is separated from AIMP3, a tumor suppressor that binds to MRS, and the released AIMP3 moves into the nucleus to repair DNA. In this context, MRS can be seen as a linker that modulates the DNA damage response and translation inhibition by UV irradiation (Kwon et al., 2011).

On the other hand, despite the importance as a biomarker for ARSs including MRS, protein structures of ARSs are similar in many ways, so that the antibodies obtained from immunization of animals show cross-reactivity to other ARSs and in many cases, high-sensitivity antibodies are not even produced. Antibodies of the present invention are expected to be of high diagnostic and industrial availability as well as for research in view of their excellent sensitivity and no cross-reactivity among different ARSs.

DETAILED DESCRIPTION OF THE INVENTION

Technical Problem

Accordingly, the present inventor found out that the antibodies generated by the antibody production method using hybridoma cells do not have cross-reactivity with other ARSs and bind specifically to MRS, thereby completing the present invention.

Thus, an aspect of the present invention is to provide an antibody or a fragment thereof which specifically binds to a peptide fragment defined by the $861^{st}$ to $900^{th}$ amino acid residues of human-derived methionyl-tRNA synthetase (MRS) protein as set forth in SEQ ID NO: 1.

Another aspect of the present invention is to provide a polynucleotide encoding the said antibody or the fragment thereof, a recombinant expression vector comprising the said polynucleotide, and a cell transformed with the said recombinant expression vector.

Another aspect of the present invention is to provide a method for the preparation of a monoclonal antibody which binds to a human-derived MRS (methionyl-tRNA synthetase) comprising:

(a) administering a cell producing the said antibody into the peritoneum of a mouse;

(b) collecting a peritoneal fluid from the mouse with inflated peritoneum; and (c) isolating a monoclonal antibody which binds specifically to MRS from the peritoneal fluid.

Another aspect of the present invention is to provide a method for the specific detection of human-derived MRS (methionyl-tRNA synthetase) protein, the method comprising contacting the said antibody or the fragment thereof with a biological sample and detecting the antibody or the fragment thereof.

Another aspect of the present invention is to provide a composition for diagnosis of a cancer comprising the said antibody or the fragment thereof as an active ingredient.

Another aspect of the present invention is to provide a composition for diagnosis of a cancer consisting of the said antibody or the fragment thereof.

Another aspect of the present invention is to provide a composition for diagnosis of a cancer consisting essentially of the said antibody or the fragment thereof.

Another aspect of the present invention is to provide use of the said antibody or the fragment in the preparation of a cancer diagnostic agent.

Another aspect of the present invention is to provide a method for diagnosis of a cancer in a subject, the method comprising administering an effective amount of the said antibody or the fragment thereof to a subject in need thereof.

Technical Solution

An embodiment according to an aspect of the present invention provides an antibody or a fragment thereof which specifically binds to a peptide fragment defined by the $861^{st}$ to $900^{th}$ amino acid residues of a human-derived methionyl-tRNA synthetase (MRS) protein as set forth in SEQ ID NO: 1.

An embodiment according to another aspect of the present invention provides a polynucleotide encoding the said antibody or the fragment thereof, a recombinant expression vector comprising the said polynucleotide, and a cell transformed with the said recombinant expression vector.

An embodiment according to another aspect of the present invention provides a method for the preparation of a monoclonal antibody which binds to a human-derived MRS (methionyl-tRNA synthetase) comprising:

(a) administering a cell producing the said antibody into the peritoneum of a mouse;

(b) collecting a peritoneal fluid from the mouse with inflated peritoneum; and (c) isolating a monoclonal antibody which binds specifically to MRS from the peritoneal fluid.

An embodiment according to another aspect of the present invention provides a method for the specific detection of human-derived MRS (methionyl-tRNA synthetase) protein comprising contacting the said antibody or the fragment thereof with a biological sample and detecting the antibody or the fragment thereof.

An embodiment according to another aspect of the present invention provides a composition for diagnosis of a cancer comprising the said antibody or the fragment thereof as an active ingredient.

And an embodiment according to another aspect of the present invention provides a composition for diagnosis of a cancer consisting of the said antibody or the fragment thereof.

And an embodiment according to another aspect of the present invention provides a composition for diagnosis of a cancer consisting essentially of the said antibody or the fragment thereof.

An embodiment according to another aspect of the present invention provides use of the said antibody or the fragment in the preparation of a cancer diagnostic agent.

An embodiment according to another aspect of the present invention provides a method for diagnosing a cancer in a subject, the method comprising administering an effective amount of the said antibody or the fragment thereof to a subject in need thereof.

Hereinafter, the present invention will be described in detail.

The present invention provides an antibody or a fragment thereof which specifically binds to a peptide fragment defined by the $861^{st}$ to $900^{th}$ amino acid residues of human-derived methionyl-tRNA synthetase (MRS) protein as set forth in SEQ ID NO: 1.

In the present invention, 'MRS (methionyl-tRNA synthetase)' is one of ARSs, which is the most important enzyme for initiating transcription and transferring methionine (Met) to tRNA. MRS increases ribosomal RNA synthesis in the nucleus and interacts with various signaling agents such as mTORC1, GCN2, CDK4, and VEGFR. When UV damages DNA, MRS is released from aminoacyl-tRNA synthetase-interacting multifunctional protein 3 (AIMP3), which binds to damaged DNA and regulates transcription.

In the present invention, 'antibody' refers to a glycoprotein comprising at least two heavy (H) chains and two light (L) chains connected to each other by disulfide bonds. Each heavy chain consists of a heavy chain variable region (hereinafter abbreviated as HCVR or VH) and a heavy chain constant region. The heavy chain constant region consists of three domains, CH1, CH2 and CH3. Each light chain consists of a light chain variable region (hereinafter abbreviated as LCVR or VL) and a light chain constant region. The light chain constant region consists of one domain, CL. VH and VL regions can be further subdivided into hypervariable regions (called complementarity determining regions (CDRs)) interspersed with more conserved regions called framework regions (FR). Each of VH and VL consists of three CDRs and four FRs arranged from amino-terminus to carboxy-terminus in the following sequence: FR1, CDR1, FR2, CDR2, FR3, CDR3, FR4. The variable regions of the heavy and light chains contain binding domains that interact with the antigen. The constant region of the antibody may mediate the binding of immunoglobulins of host tissues or factors, including various cells of the immune system (e.g. effector cells) and the first component of the traditional complementary system (C1q).

1E8 and 8A12 antibodies of the present invention specifically bind to the peptide fragments comprising amino acid sequence from the $861^{st}$ to $900^{th}$ amino acid residues of human-derived MRS protein. Preferably, regarding the area of human-derived MRS protein where 1E8 antibody and 8A12 antibody of the present invention bind to, a specific sequence is not particularly limited as long as it is a contiguous region comprising the amino acid sequence represented by SEQ ID NO:39. Usually it may be a fragment which includes the amino acid sequence of SEQ ID NO:39 and consists of 40 to 900 amino acid residues, more preferably, 40 to 80 amino acid residues, specifically, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 amino acid residues. Most preferably, it may be the amino acid sequence represented by SEQ ID NO:39 derived from human MRS protein.

In one embodiment of the invention, fragments were prepared corresponding to the position of $598^{th}$~$900^{th}$ aa (SEQ ID NO:46), $660^{th}$~$860^{th}$ aa (SEQ ID NO: $660^{th}$~$900^{th}$ aa (SEQ ID NO:48), $730^{th}$~$900^{th}$ aa (SEQ ID NO:49) of MRS protein. Each fragment was cloned and subjected to western blot. As a result, fragments of SEQ ID NOs: 46, 48, and 49 were recognized by the antibody, but the fragment of SEQ ID NO:47 was not recognized. Through this, it was confirmed that 1E8 antibody and 8A12 antibody of the present invention specifically binds to the fragment of the $861^{th}$ to $900^{th}$ amino acid residues (SEQ ID NO:39) of human-derived MRS protein (see FIG. 6b).

'An antibody or a fragment thereof that specifically binds to human-derived MRS (methionyl-tRNA synthetase) protein' provided by the present invention is characterized by comprising an antibody light chain variable region (VL) comprising a light chain complementarity determining region 1 (CDR1) comprising an amino acid sequence as set forth in SEQ ID NO:3 or SEQ ID NO:15; a light chain complementarity determining region 2 (CDR2) comprising an amino acid sequence as set forth in SEQ ID NO:5 or SEQ ID NO:17; a light chain complementarity determining region 3 (CDR3) comprising an amino acid sequence as set forth in SEQ ID NO:7 or SEQ ID NO:19 and an antibody heavy chain variable region (VH) comprising a heavy chain complementarity determining region 1 (CDR1) comprising an amino acid sequence as set forth in SEQ ID NO:9 or SEQ ID NO:21; a heavy chain complementarity determining region 2 (CDR2) comprising an amino acid sequence as set forth in SEQ ID NO:11 or SEQ ID NO:23; a heavy chain complementarity determining region 3 (CDR3) comprising an amino acid sequence as set forth in SEQ ID NO:13 or SEQ ID NO:25.

The antibody or the fragment thereof that specifically binds to human-derived MRS (methionyl-tRNA synthetase) protein according to the present invention preferably comprises the following CDR compositions of VH and LH, which represent the CDR combinations of 1E8 antibody and 8A12 antibody of Examples in (i) and (ii) respectively:

(i) an antibody light chain variable region (VL) comprising the light chain complementarity determining region 1 (CDR1) comprising the amino acid sequence of SEQ ID NO:3, the light chain complementarity determining region 2 (CDR2) comprising the amino acid sequence of SEQ ID NO:5, and the light chain complementarity determining region 3 (CDR3) comprising the amino acid sequence of SEQ ID NO:7, and an antibody heavy chain variable region (VH) comprising the heavy chain complementarity determining region 1 (CDR1) comprising an amino acid sequence of SEQ ID NO:9, the heavy chain complementarity determining region 2 (CDR2) comprising the amino acid sequence of SEQ ID NO:11, and the heavy chain complementarity determining region 3 (CDR3) comprising the amino acid sequence of SEQ ID NO:13;

(ii) an antibody light chain variable region (VL) comprising the light chain complementarity determining region 1 (CDR1) comprising the amino acid sequence of SEQ ID NO:15, the light chain complementarity determining region 2 (CDR2) comprising the amino acid sequence of SEQ ID NO:17, and the light chain complementarity determining region 3 (CDR3) comprising the amino acid sequence of SEQ ID NO:19, and an antibody heavy chain variable region (VH) comprising the heavy chain complementarity determining region 1 (CDR1) comprising an amino acid sequence of SEQ ID NO:21, the heavy chain complementarity determining region 2 (CDR2) comprising the amino acid sequence of SEQ ID NO:23, and the heavy chain complementarity determining region 3 (CDR3) comprising the amino acid sequence of SEQ ID NO:25.

Most preferably, the antibody or the fragment thereof according to the present invention is characterized by comprising an antibody light chain variable region comprising the amino acid sequence of SEQ ID NO:27 (IE8 VL) or SEQ ID NO:31 (8A12 VL) and an antibody heavy chain variable region comprising the amino acid sequence of SEQ ID NO:29 (IE8 VH) or SEQ ID NO:32 (8A12 VH)

The antibody according to the present invention is not limited in kind as long as it has the above CDR combination or VH and VL combination. Specifically, the antibody may be selected from the group consisting of IgG, IgA, IgM, IgE, and IgD, and preferably an IgG antibody.

The antibody of the present invention may be a monoclonal antibody or a polyclonal antibody as long as it has the above CDR combination or the VH and VL combination which specifically binds to human-derived MRS protein. However, it is preferable to be a monoclonal antibody, which is a population of antibodies having substantially identical amino acid sequences of heavy and light chains.

The antibody of the invention can be derived from any animal, including mammals, birds, and the like, including humans. Preferably, the antibody may be an antibody of human, mouse, donkey, sheep, rabbit, goat, guinea pig, camel, horse or chicken. More preferably, it may be a human-derived or chimeric antibody comprising a part of an antibody derived from a human and another part of an antibody derived from an animal of a different species. That is, the present invention includes a chimeric antibody, humanized antibody, and human antibody, and preferably may be a human antibody.

A human antibody is the antibody having the amino acid sequence of human immunoglobulins, including an antibody isolated from human immunoglobulin libraries or isolated from animals transfected with one or more human immunoglobulins and not expressing endogenous immunoglobulins (U.S. Pat. No. 5,939,598).

In addition, the fragment of the antibody in the present invention means a fragment of an antibody that retains the antigen specific binding capacity of the whole antibody, preferably the fragment maintains at least 20%, 50%, 70%, 80%, 90%, 95% or 100% or more of the MRS binding affinity of the parent antibody. Specifically, it may be in the form of Fab, F (ab)2, Fab', F(ab')2, Fv, diabody, scFv and the like.

A Fab (fragment antigen-binding) is an antigen-binding fragment of the antibody, consisting of one variable domain and a constant domain of each of the heavy and light chains. A F(ab')2 is a fragment produced by hydrolyzing an antibody with pepsin, in which two Fabs are linked by disulfide bonds at the heavy chain hinges. A F(ab') is a monomer antibody fragment in which a heavy chain hinge is added to a Fab separated by reducing the disulfide bond of the F(ab')2 fragment. A Fv (variable fragment) is an antibody fragment consisting of only the variable region of each of the heavy and light chains. A single chain variable fragment (scFv) is a recombinant antibody fragment in which a heavy chain variable region (VH) and a light chain variable region (VL) are linked by a flexible peptide linker. A diabody refers to a fragment in which VH and VL are linked to each other by a very short linker and unable to bind to each other, thereby forming a dimer by combining with VL and VH of another scFv of the same form. For the purposes of the present invention, the antibody or the fragment thereof is not limited in structure or form as long as they retain binding specificity for human-derived MRS protein.

In addition, the above-described antibody or the fragment thereof of the present invention may be conjugated to enzymes, fluorescent materials, radioactive materials and proteins, but are not limited thereto. Furthermore, methods of conjugating such materials to antibodies are well known in the art.

The present invention provides a polynucleotide encoding the said antibody or the fragment thereof.

Polynucleotides may also be described herein as oligonucleotides or nucleic acids, and include DNA molecules (for example, cDNA or genomic DNA, RNA molecules such as mRNA), analogues of DNA or RNA synthesized using nucleotide analogs (for example, peptide nucleic acids and non-naturally occurring nucleotide analogues) and hybrids thereof. These polynucleotides may be single-stranded or double-stranded.

The said polynucleotide means a nucleotide sequence encoding an antibody consisting of heavy and light chains having the CDR combinations or VH and VL combinations which binds to MRS protein. The polynucleotide of the present invention is not particularly limited in sequence as long as it encodes the antibody or the fragment thereof of the present invention. The polynucleotide encoding the above-mentioned CDR sequences of the antibody according to the present invention described above is not particularly limited in sequence, but preferably may include the DNA sequences represented by SEQ ID NO:4 (light chain CDR1), SEQ ID NO:6 (light chain CDR2), SEQ ID NO:8 (light chain CDR3), SEQ ID NO:10 (heavy chain CDR1), SEQ ID NO:12 (heavy chain CDR2), SEQ ID NO:14 (heavy chain CDR3), SEQ ID NO:16 (light chain CDR1), SEQ ID NO:18 (light chain CDR2), SEQ ID NO:20 (light chain CDR3), SEQ ID NO:22 (heavy chain CDR1), SEQ ID NO:24 (heavy chain CDR2), or SEQ ID NO:26 (heavy chain CDR3).

In addition, the polynucleotide encoding the above-mentioned VH and VL of the antibody according to the present invention is not particularly limited in sequence, but preferably may contain the DNA sequence represented by SEQ ID NO:28 (VL), SEQ ID NO:30 (VH), SEQ ID NO:32 (VL) or SEQ ID NO:34 (VH)

The polynucleotide encoding the antibody or the fragment thereof of the present invention can be obtained by methods well known in the art. For example, it can be synthesized by employing oligonucleotide synthesis techniques well known in the art, such as polymerase chain reaction (PCR), or the like, based on DNA sequences or corresponding amino acid sequences encoding portions or all of the heavy and light chains of the antibody.

The present invention provides a recombinant expression vector comprising the said polynucleotide encoding the said antibody or the fragment thereof.

In the present invention, the 'recombinant' may be used interchangeably with 'genetic manipulation', and means making a gene of a nonexistent form in a natural state using molecular cloning experiment techniques such as modifying, cutting, and linking genes.

In the present invention, 'expression' means production of protein or nucleic acid in the cell.

In the present invention, a 'recombinant expression vector' is a vector capable of expressing a protein or nucleic acid (RNA) of interest in a suitable host cell, referring to a genetic construct containing essential regulatory elements operably linked to allow the expression of a polynucleotide (gene) insert. 'Operably linked' refers to a functional linkage between a nucleic acid expression control sequence and a nucleic acid sequence encoding a protein or RNA of interest to perform a general function, meaning linked such that a gene can be expressed by an expression control sequence. The expression control sequence refers to a DNA sequence that controls the expression of a polynucleotide sequence operably linked in a particular host cell. Such regulatory sequences include promoters for performing transcription, any operator sequences for controlling transcription, sequences encoding suitable mRNA ribosomal binding sites, sequences controlling termination of transcription and translation, initiation codons, termination codons, polyadenylation signal and enhancer, etc.

The recombinant expression vector of the present invention is not particularly limited as long as it is a vector commonly used in the cloning field, and examples thereof include, but are not limited to, a mammalian expression vector, plasmid vector, cosmid vector, bacteriophage vector, and viral vector. The plasmid includes *E. coli*-derived plasmids (pBR322, pBR325, pUC118 and pUC119, pET-22b (+)), *Bacillus subtilis*-derived plasmids (pUB110 and pTP5) and yeast-derived plasmids (YEp13, YEp24 and YCp50).

The virus may be an animal virus such as a retrovirus, adenovirus or vaccinia virus, or an insect virus such as baculovirus, or the like.

Therefore, the recombinant expression vector according to the present invention means a genetic construct operably linked to express the polynucleotide encoding the antibody or the fragment thereof consisting of the heavy and light chains comprising the combinations of the above-mentioned CDR or VH and VL which can specifically bind to human-derived MRS protein in an appropriate host cell.

The polynucleotides encoding the heavy and light chains of the antibody according to the present invention may be included separately in different recombinant expression vectors, or may be contained in one single recombinant expression vector.

The present invention provides a cell transformed with the said recombinant expression vector.

The cell of the present invention is not particularly limited as long as it is a cell that can be used to express a polynucleotide encoding the antibody or the fragment thereof contained in the recombinant expression vector of the present invention. Cells (host cells) transformed with the recombinant expression vector according to the present invention may be prokaryotic (e.g., *E. coli*), eukaryotic (e.g., yeast or other fungus), plant cells (e.g., tobacco or tomato plant cells), animal cells (e.g., human cells, monkey cells, hamster cells, rat cells, mouse cells), insect cells, or hybridomas derived therefrom. Preferably, cells may be derived from a mammal including a human.

The term 'transformation' refers to the modification of the genotype of a host cell by the introduction of an exogenous polynucleotide, and refers to the introduction of the exogenous polynucleotide into the host cell regardless of the method used for transformation. Exogenous polynucleotides introduced into a host cell can be maintained as integrated in the genome of the host cell or without integration, both of which are within the scope of the present invention.

The recombinant expression vector capable of expressing the antibody or the fragment thereof that specifically binds to human-derived MRS protein according to the invention can be delivered into and transform a cell to produce the antibody or the fragment thereof by methods known in the art, such as, but not limited to, transient transfection, microinjection, transduction, cell fusion, calcium phosphate precipitation, liposome-mediated transfection, DEAE dextran-mediated transfection, polybrene-mediated transfection, electroporation, gene gun and the like.

The present invention provides a method for the preparation of a monoclonal antibody which binds to human-derived MRS (methionyl-tRNA synthetase) comprising: (a) administering a cell producing the said antibody into the peritoneum of a mouse; (b) collecting a peritoneal fluid from the mouse with inflated peritoneum; and (c) isolating a monoclonal antibody which binds specifically to MRS from the peritoneal fluid.

The transformed cell of the present invention may be a hybridoma cell expressing the antibody of the fragment thereof of the present invention.

In one embodiment of the present invention, myeloma cells and B cells of mice immunized against MRS were fused by treatment with PEG and incubated in HT medium for 3 hours at 37° C. and 5% $CO_2$ in the incubator (see Examples 1~3).

The present invention provides a method for the specific detection of human-derived MRS (methionyl-tRNA synthetase) protein comprising contacting the said antibody or the fragment thereof with a biological sample and detecting the antibody or the fragment thereof.

Since the antibody or fragment thereof of the present invention specifically binds to human-derived MRS protein, it is useful in diagnostic assays for detecting and quantifying MRS proteins, for example in specific cells, tissues, or serum.

The detection method of the present invention may comprise a step (step (1)) for preparing a sample to measure the presence and concentration of MRS using the antibody or the fragment thereof according to the present invention before contacting the antibody or the fragment thereof according to the present invention with a biological sample.

A person skilled in the art can appropriately select a known method for detecting proteins using an antibody, and prepare a sample suitable for the selected method. The method of detecting proteins using the antibody can be, not limited hereto, for example, western blot, immunoblot, dot blot, immunohistochemistry, immunocytochemistry, enzyme-linked immunosorbent assay (ELISA), radioimmunoassay, competitive binding assay, and immunoprecipitation. For example, in order to perform western blot, a sample or cell lysate may be prepared by adding a buffer suitable for electrophoresis and boiling, and for immunohistochemical staining and immunocytochemical staining, pretreatment such as fixing cells or organ sections and blocking can be carried out.

Then the next step (step (2)) is performed by contacting the antibody or the fragment according to the present invention with the sample prepared in the previous step.

The antibody according to the present invention comprises the compositions of CDR, or VH and VL as described above. Specific kinds or sequence compositions are as previously explained regarding the antibody or the fragment thereof binding specifically to human-derived MRS protein.

The antibody or the fragment thereof may be labeled with a generally detectable moiety for its 'detection'. For example, using techniques described in the literature [Current Protocols in Immunology, Volumes 1 and 2, 1991, Coligen et al., Ed. Wiley-Interscience, New York, N.Y., Pubs], it can be labeled with radioisotopes or fluorescent labels. Or various enzyme-substrate labels are available, examples of which include luciferases such as Drosophila luciferase and bacterial luciferase (U.S. Pat. No. 4,737,456), luciferin, 2,3-dihydrophthalazine diones, malate dehydrogenase, urase, peroxidase such as horseradish peroxidase (HRPO), alkaline phosphatase, β-galactosidase, glucoamylase, lysozyme, saccharides oxidases (e.g. glucose oxidase, galactose oxidase, and glucose-6-phosphate dehydrogenase), heterocyclic oxidases (e.g. uricase and xanthine oxidase), lactoperoxidase, microperoxidase and the like. Techniques for conjugating enzymes to antibodies are described, for example, in the literature [O'Sullivan et al., 1981, Methods for the Preparation of Enzyme-Antibody Conjugates for use in Enzyme Immunoassay, in Methods in Enzym. (J. Langone & H. Van Vunakis, eds.), Academic press, N.Y., 73: 147-166]. Labels can be conjugated directly or indirectly to antibodies using a variety of known techniques. For example, an antibody can be conjugated to biotin and any labels belonging to the three broad categories mentioned above can be conjugated with avidin and vice versa. Biotin binds selectively to avidin and thus the label can be conjugated to the antibody in this indirect manner. Alternatively, to achieve indirect conjugation of the label to an antibody, the antibody may be conjugated with a small hapten (e.g. digoxin) and one of the different types of labels mentioned above can be conjugated with anti-Hapten antibodies (e.g., anti-digoxin antibodies). Thus, indirect conjugation of the label to an antibody can be achieved.

In the present invention, 'contacting' is used in its general sense, and means to mix, bond, or about two or more materials. Such contact may be carried out in vitro or in another container, and may also be performed in situ, in vivo, in an individual, in a tissue, or in a cell.

Next, the step (step (3)) of detecting the antibody or the fragment thereof according to the present invention is performed after the step (2).

The 'detection' or 'detecting' is with regards to a complex formed in the sample by the antibody or the fragment thereof according to the present invention and its antigen, and means to detect the presence or absence of MRS protein or to measure the level of the protein (qualitative and/or quantitative measurement). Therefore, after performing step (2) and before the detection step (step (3)) described below, a step of removing extra antibody or fragment thereof that do not form complex with human-derived MRS protein may be further included.

When the antibody or the fragment thereof used in step (2) described above contains a detectable moiety, such as direct labeling with fluorescence, radioisotopes, enzymes, or the like, detection can be performed accordingly by a method known in the art. In one example, radioactivity can be measured, for example, by scintillation counting, and fluorescence can be quantified using a fluorimeter.

In addition, when the antibody or the fragment thereof used in step (2) described above does not include the aforementioned detection moiety in itself, it can be indirectly detected using a secondary antibody labeled with fluorescence, radioactivity, enzyme, or the like, as known in the art, may be used. The secondary antibody binds to an antibody according to the invention or the fragment thereof (primary antibody).

The present invention provides a composition for diagnosis of a cancer comprising the said antibody or the fragment thereof as an active ingredient.

The present invention provides a composition for diagnosis of a cancer consisting of the said antibody or the fragment thereof.

The present invention provides a composition for diagnosis of a cancer consisting essentially of the said antibody or the fragment thereof.

In the present invention, the cancer is not particularly limited as long as it is known in the art as a malignant tumor, preferably may be a lung cancer, pancreatic cancer or biliary tract cancer.

Diagnosis of a cancer according to the invention can be carried out by detecting MRS proteins in a biological sample.

In the present invention, the term 'diagnosis' or 'diagnosing' means to check the presence or characteristics of a pathological state. In the present invention, the said diagnosis is to determine whether a cancer, etc. is developed or possible to develop (risk).

In the present invention, the 'cancer' may be a biliary tract cancer, breast cancer, colon cancer, lung cancer, small cell lung cancer, stomach cancer, liver cancer, blood cancer, bone cancer, pancreatic cancer, skin cancer, head or neck cancer, skin or intraocular melanoma, uterine cancer, ovarian cancer, rectal cancer, anal cancer, colon cancer, breast cancer, Fallopian tube carcinoma, endometrial carcinoma, cervical cancer, vaginal cancer, vulvar carcinoma, Hodgkin's disease, esophageal cancer, small intestine cancer, endocrine gland cancer, thyroid cancer, parathyroid cancer, adrenal cancer, soft tissue sarcoma, urethral cancer, penis cancer, prostate cancer, chronic or acute leukemia, lymphocytic lymphoma, bladder cancer, kidney or ureter cancer, renal cell carcinoma, renal pelvic carcinoma, CNS tumor, primary CNS lymphoma, spinal cord tumor, brainstem glioma or pituitary adenoma. More preferably, the cancer may be a lung cancer, pancreatic cancer, or biliary tract cancer.

In the present invention, the term 'detection' is as described above, and the biological sample includes blood and other liquid samples of biological origin, solid tissue samples such as biopsy samples and tissue cultures or cells derived therefrom. More specifically, for example, but not limited to, tissues, extracts, cell lysates, whole blood, plasma, serum, saliva, ocular fluid, cerebrospinal fluid, sweat, urine, milk, ascites fluid, synovial fluid, peritoneal fluid, and the like. The sample can be obtained from an animal, preferably a mammal, most preferably a human. The sample may be pretreated before use for the detection. For example, pretreatment may include filtration, distillation, extraction, concentration, inactivation of inhibitory components, addition of reagents, and the like. In addition, nucleic acids and proteins can be isolated from the sample and used for detection.

The antibody or the fragment thereof according to the present invention may be provided as a diagnostic kit, and the kit is not particularly limited in kind as long as it is known in the art as an assay kit for providing an antibody or a peptide having a specific binding domain as a component. Examples include western blot, ELISA, radioimmunoassay, radioimmunodiffusion assay, oukteroni immunodiffusion, rocket immunoelectrophoresis, tissue immunostaining, immunoprecipitation assay, complement fixation assay, kit for FACS or protein chip, and the like.

The antibody or the fragment thereof of the present invention can be used in packaged combinations of reagents in predetermined amounts along with instructions for use in the kit, i.e., diagnostic kits for performing diagnostic assays. If the antibody is labeled with an enzyme, the kit may include cofactors required by the enzyme as substrate precursors to provide the substrate and chromophores or fluorophores. In addition, other additives may be included such as stabilizers, buffers (e.g., blocking buffers or lysis buffers), and the like. The relative amounts of the various reagents can be changed widely to provide a concentration in solution of the reagent that fully optimizes the sensitivity of the assay. Reagents may be provided as generally lyophilized dry powder, which will contain an excipient that will provide a reagent solution with an appropriate concentration upon dissolution.

In one embodiment of the present invention, MRS-AIMP3 protein was prepared using $E.\ coli,$ and injected into the mouse abdominal cavity for immunization, and blood and B cells were extracted from the immunized mouse. Next, hybridoma cells were prepared by fusion of PEG-treated B cells and myeloma cells, and screened by ELISA and western blot to select those recognize only MRS. Finally '1E8' and '8A12' clones were obtained (see Example 1).

In another embodiment of the present invention, those hybridoma cells were administered into the mouse abdominal cavity. Then, when the abdominal cavity of the mouse was filled with ascites, the ascites were extracted by syringe, and only the supernatant was separated after centrifugation. Protein A was then filled into the column and washed, then the ascites solution was diluted with phosphate buffer and loaded onto the Protein A column and each fraction was eluted (see Example 2).

In another embodiment of the present invention, 1E8 antibody and 8A12 antibody obtained from the hybridoma cells were diluted 1:5000, and used for western blot of the cell eluates of H460 cells treated with si-MRS. As a result, it was confirmed that both 1E8 antibody and 8A12 antibody bind to MRS, and these antibodies specifically recognize MRS based on treatments using two kinds of si-MRS (see Example 3-1 and FIG. 1).

In another embodiment of the present invention, 96-well plate was coated with His-MRS, MRS full, DX2 tag free, 34S-DX2, 34S-AIMP2, His-CRS, His-AIMP1, His-GRS, His-WRS and His-KRS and used for ELISA using 1E8 antibody and 8A12 antibody. As a result, it was confirmed that 1E8 antibody (FIGS. 2*a*) and 8A12 antibody (FIG. 2*b*) bind only to MRS and did not react to other ARS and AIMP proteins (see Example 3-2, FIG. 2*a* and FIG. 2*b*).

In another embodiment of the present invention, the surface plasmon resonance (SPR) experiments using 1E8 antibody and 8A12 antibody and MRS+AIMP3 protein showed that 1E8 antibody (FIGS. 3*a* and 3*b*) and 8A12 antibody (FIGS. 4*a* and 4*b*) bind to MRS+AIMP3 protein but not to the same AIMP3 protein, thus confirming high affinity of the anti-MRS antibody (Examples 3-3, 3a, 3b, 4a and 4b).

In another embodiment of the present invention, Panc-1 cells cultured on the cover glass were treated and reacted with 1E8 antibody and 8A12 antibody diluted 1:200 followed by the secondary antibody diluted 1:200. DAPI staining and fluorescence microscopy showed that 1E8 and 8A12 antibodies obtained in the present invention bind to the surface of Panc-1 cells (see Example 4 and FIG. 5).

In another embodiment of the present invention, six fragments of different lengths and positions were prepared from MRS protein, cloned into a vector, and transfected into H640 cells and transfectants were cultured. Then, proteins were collected from the cells and subjected to western blot using 1E8 antibody and 8A12 antibody. As a result, it was confirmed that both 1E8 and 8A12 antibody combined with fragment 5 (598~900 aa) and fragment 6 (298~900 aa) (see FIG. 6*a*). Subsequently, 598~900 aa portion of MRS protein was prepared as four different fragments and subjected to western blot in the same manner as described above. As a result, it was confirmed that both 1E8 antibody and 8A12 antibody bound to fragment 5 (598~900 aa), fragment 8 (600~900 aa), fragment 9 (730~900 aa) (see Example 5, FIG. 6A and FIG. 6B).

The present invention provides use of the said antibody or the fragment in the preparation of a cancer diagnostic agent.

The present invention provides a method for diagnosing a cancer in a subject, the method comprising administering an effective amount of the said antibody or the fragment thereof to a subject in need thereof.

The term 'effective amount' of the present invention refers to an amount that exhibits an effect of improving, treating, preventing, detecting, or diagnosing cancer when administered to an individual or an subject, and the term 'subject' includes an animal, preferably a mammal, particularly a human. It may be an animal, or may be a cell, tissue, organ or the like derived from the animal. The subject may be a patient in need of the said effect.

The term 'diagnosis' or 'diagnosing' of the present invention refers comprehensively to identifying a condition, a presence or a characteristic of a cancer or a cancer-related disease, and includes identifying whether or not a cancer or a cancer-related disease is developed or possible to develop (risk). However, it is not limited thereto.

The term 'comprising' of the present invention is used in the same way as 'including' or 'characterized by' and does not exclude additional component elements or method steps not mentioned in terms of any particular composition or method. The term 'consisting of' means to exclude additional elements, steps or components, etc., unless otherwise noted. The term 'essentially consisting of' means within the scope of the composition or method, including the component elements or steps described, as well as the component elements or steps that do not substantially affect its basic properties, and the like.

Advantageous Effect

Therefore, the antibody or the fragment thereof of the present invention can be utilized to diagnose a MRS-associated cancer because it binds specifically to human-derived MRS with no cross-reactivity with different proteins including the same ARS family, allowing a specific MRS detection

BRIEF DESCRIPTION OF DRAWINGS/FIGURES

MODE FOR CARRYING OUT INVENTION

Figure 1:
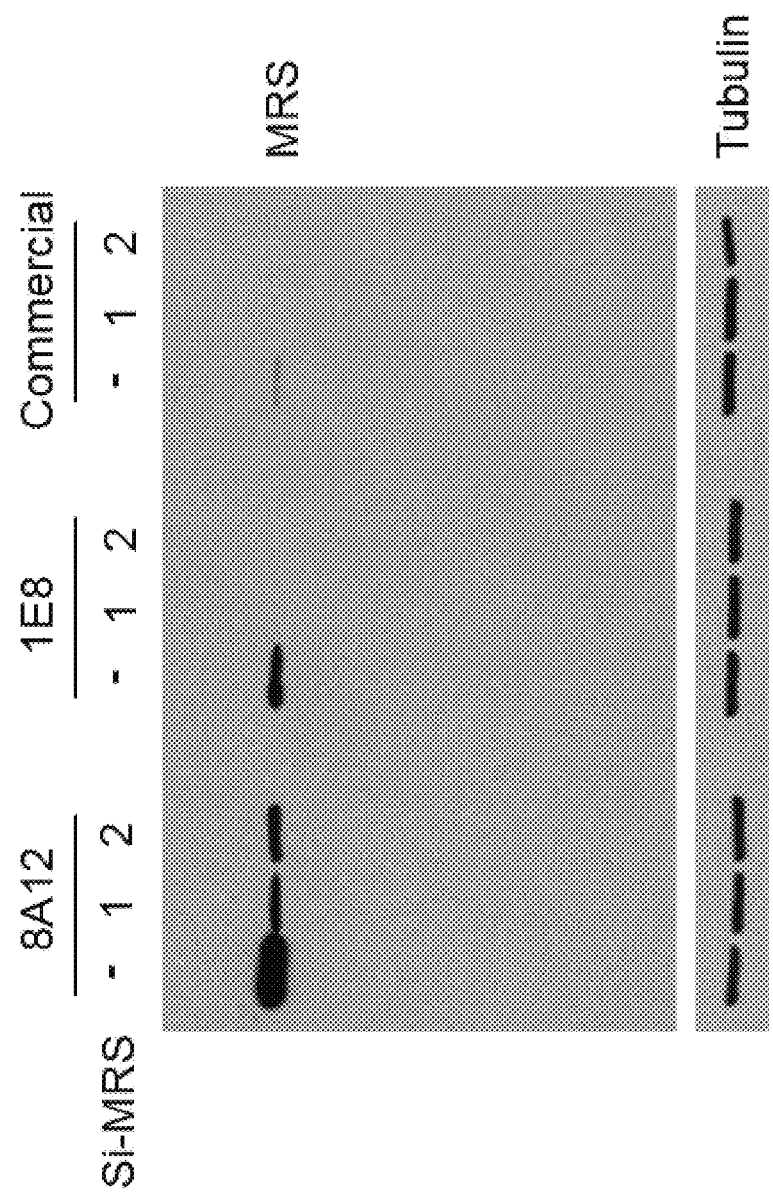
FIG. 1 shows the results of western blot to confirm the binding of MRS antibodies (1E8, 8A12) to MRS protein using the cell elutes of si-MRS treated H460 cells.

Hereinafter, the present invention will be described in more detail with reference to examples, experimental examples and manufacturing examples. However, the following examples, experimental examples and preparation examples are illustrative of the present invention, and the present invention is not limited to the following examples, experimental examples and manufacturing examples.

<Experimental Methods>
Cell Culture
Each of 293T, H460 and Panc-1 cells were cultured in DMEM medium and cells with passages 5 to 9 were used. Different cell lines were incubated in RPMI-1640 (Hyclone, GE lifesciences) and DMEM (Hyclone, GE lifesciences) media containing 10% FBS (fetal bovine serum, Hyclone, GE lifesciences), 1% penicillin (Hyclone, GE lifesciences). Cells were incubated in a condition of 5% $CO_2$, 37° C.

Animal Models
10-week-old BALB/c mice weighing 25~30 g were purchased from Orient Bio Co (Sungnam, Kyunggido, Republic of Korea). They were used in this study after sufficient acclimation under constant conditions (temperature: 20±2° C., humidity: 40~60%, 12 hour light/dark cycle) at the animal facility. Animal experiments were performed following the guidelines of the University Animal Care and Use Committee of Seoul National University.

Example 1

Selection of Cells Producing Monoclonal Antibodies Against MRS 1-1. Synthesis of MRS-AIMP3 Proteins
In order to express and purify MRS-AIMP3 (aminoacyl tRNA synthetase complex-interacting multifunctional protein 3) protein using *E. coli*, the following experiments were carried out.

BL21DE3 strain was used to transform with MRS (methionyl-tRNA synthetase, SEQ ID NO:1) and AIMP3 (NM_004280.4, SEQ ID NO:49) and a single colony was incubated in 5 ml LB media containing ampicillin until OD600 value reaches 0.6~0.8. Afterwards, 1 mM of IPTG was added thereto, followed by incubation at 37° C. for 3 hours, and centrifugation for 10 minutes to collect only cells. SDS-PAGE was performed with the cell solution and the expression was confirmed using Coomassie stain.

Subsequently, cell solution in which overexpression was induced by IPTG was collected and centrifuged to obtain cells. After resuspension with 1 ml DPBS, cells were lysed using an ultrasonicator, and centrifuged to isolate co-purified MRS-AIMP3 protein from the lysates.

1-2. Immunization of Mice
In order to obtain immunized mice required for the production of hybridoma cells, the first injections of the co-purified MRS-AIMP3 proteins obtained in Example 1-1 were administered intraperitoneally to four 8-10 week old mice. Two weeks later, the second injections with the same dose of the co-purified MRS-AIMP3 proteins were made into the abdominal cavity of mice in order to increase the immunity of the mice after the first immunization. One week later, three days before the cell fusion experiment, the co-purified MRS-AIMP3 proteins were injected into the tail vein of mice as a booster.

Those immunized mice were anesthetized with ether and blood was drawn from the heart with a heparinized syringe. Collected blood was left overnight at 4° C. and centrifuged to separate serum. Separated serum was properly and stored at −80° C.

1-3. Preparation of Hybridoma Cells
First, myeloma cells were prepared for cell fusion. Myeloma cells were cultured and adjusted the cell density to 2.5~5.0×10$^4$/ml. 24 hours prior to cell fusion, myeloma cells were diluted by ⅓. The immunized mice in Example 1-2 were anesthetized with ether and spleens were collected. B cells were isolated, washed with SF-DMEM2 (DMEM+2× AA) and eluted. Cell suspension was collected, placed in a tube and allowed to settle down. Supernatant was transferred to a new tube and centrifuged for 5 minutes at 1500 rpm. Supernatant of the centrifuged splenocytes was removed and tapped before filling with SF-DMEM2. B cells and myeloma cells were respectively centrifuged and washed and washing was repeated one more time. Supernatant of the washed myeloma cells was removed, and cells were tapped before filling with SF-DMEM2. In addition, after removing supernatant of the washed B cells and tapping, red blood cells (RBC) were added to 1 ml of LB (lysis buffer), followed by filling with SF-DMEM2. Then, B cells and myeloma cells were centrifuged, respectively, and supernatant was removed, tapped and filled with 10 ml of SF-DMEM2. Cell concentration was determined by counting the B cells and myeloma cells diluted by 100 fold in e-tubes, respectively [concentrations of B cells ($1\times10^8$, $8\times10^7$, $5\times10^7$), and myeloma cells ($1\times10^7$, $8\times10^6$, $5\times10^6$). The ratio of B cells and myeloma cells was determined to be 10:1. B cells and myeloma cells of the determined concentrations were put together in a tube and centrifuged. Supernatant of the centrifuged cells was removed and then semi-dried by placing on an alcohol pad and tapped for 30 seconds to 1 minute. Here, PEG (2 ml) was added slowly by pipetting and reacted for 1 minute, and SF-DMEM2 was added while shaking the tube and centrifuged. After centrifugation, supernatant was removed and, without tapping, HT media [HT50×(HT(sigma) 1 vial+SF-DMEM1 10 ml) 1 ml, FBS 10 ml, SF-DMEM1(DMEM+1×AA) 30 ml] was dropped with increasing speed and the volume was increased to 50 ml. This suspension was incubated again in an incubator at 37° C., 5% $CO_2$ for 3 hours.

1-4. Selection of Hybridoma Cells Producing Monoclonal Antibodies and Cloning

In order to select cells which recognize MRS well and do not interact with AIMP3 among the fused cell groups prepared in Examples 1-3, and to check whether antibodies were produced, the following experiments were performed.

First, medium was exchanged 8 to 9 days after cell fusion, and cells were cultured in cDMEM2 until growing well from 96 wells to 24 wells. On day 5~7 after replacing the medium, supernatant of the color-changed wells was withdrawn and filled with cDMEM2, and then subjected to ELISA test. After ELISA test, wells were selected and transferred to 24 wells for incubation. After incubation in 24 wells, ELISA test was repeated. Specifically, the concentration of the fusion cells in 24 wells was confirmed, and the fusion cells were diluted in 15 ml of culture medium at the concentration of 0.5 cell/well in a 96 well plate. Fusion cell dilutions were dispensed at 150 μl per well. Wells containing a single cell were checked by microscopic examination. Supernatant of wells where cells had grown to a certain degree was harvested and examined by ELISA and western blot to perform the first screening. Based on the first screening results, the selected fusion cells were transferred to 24 wells, cultured, centrifuged, and supernatant was collected and confirmed by ELISA and western blot for the second screening. Absorbance (OD value) of the fusion cells grown in 24 wells was confirmed by ELISA, and only those with absorbance value greater than 1.0 were selected and transferred to a 25T/C culture flask, incubated, and centrifuged, and supernatant was collected and examined by ELISA and western blot for the third screening. Fusion cells selected based on the third screening results were then transferred to a 75T/C culture flask, cultured, and absorbance was confirmed by ELISA to select cells that recognize only MRS well and not AIMP3. Finally, clones "1E8" and "8A12" were secured.

Example 2

Production of Monoclonal Antibodies Against MRS and Purification 2-1. Hybridoma Cell Culture and Production of Monoclonal Antibodies Against MRS From the finally selected fusion cells (hybridoma cells, "1E8" and "8A12") in Example 1, following two methods can be used to obtain, respectively.

1) 500 μl of pristane was injected into the abdominal cavity of female mice at 7 to 8 weeks of age. Fusion cells cultured in a 75T/C culture flask were collected, centrifuged, and pipetted in phosphate buffer after removing supernatant. After 7-10 days of pristane administration, the fusion cells selected in Example 1-4 were injected intraperitoneally to mice at $8\times10^5\sim4\times10^7$, respectively. After 1-2 weeks when the mouse peritoneum is filled with ascites, the ascites was drawn using an 18G needle. The ascites was kept at 4° C. overnight and centrifuged the following day to remove the mass material including the yellow fat layer and to separate only supernatant. Isolated supernatant was aliquoted and stored at −20° C.

In order to purify antibodies from the ascites fluid, a column was filled with an appropriate amount of Protein A stored in the storage solution (20% ethanol), flushed with 20% ethanol, and washed using binding buffer (20 mM sodium phosphate, pH 7.0) of 5 bed volumes. The ascites solution was diluted in phosphate buffer in an appropriate amount and loaded onto the Protein A column. After binding with 3 bed volumes of binding buffer (20 mM sodium phosphate, pH 7.0), 0.5 mL fractions were eluted with 3 bed volumes of elution buffer (0.1M glycine buffer, pH 3.0~2.5). Each fraction was neutralized with 35 μl of neutralization buffer (1M Tris-HCl, pH 9.0). After standing overnight in 70% ethanol at refrigeration temperature, it was again stored in the storage solution (20% ethanol) until the next use. The purity of the fractions was confirmed via SDS-PAGE and desalted on Amersharm GE columns.

2) The hybridoma cells were cultured in up to 860 mL of culture media using Cellstack-5 (Corning, N.Y.). Serum-free medium (Thermo) was supplemented with 5 mM GlutaMAX (Gibco) and 1×Cholesterol lipid concentrate (Gibco) and inoculated with the cells at the initial concentration of $1.4\sim2.0\times10^5$ cell/mL. After 4~5 days of dispensing, cells were removed by centrifugation at 2000 rpm for 10 minutes to recover the supernatant. After checking pH of the supernatant, it was adjusted to pH 7.6 using the prepared 20×binding solution (1M potassium phosphate dibasic) (pH 9.0). Then it was filtered using a 0.22 um filter to obtain a neutralized antibody culture solution.

2-2. Purification of Monoclonal Antibodies Against MRS

The antibody culture solution obtained in Example 2-1 or 2-2 was purified by the following method. A column was charged with an appropriate amount of Protein A and flowed with 10 column volumes of distilled water, followed by the same amount of 1× binding solution (50 mM potassium phosphate dibasic) (pH 9.0). Then, the column was flowed with the obtained antibody culture solution to bind antibodies to Protein A, and then washed with 1× binding solution (50 mM Potassium phosphate dibasic) (pH 9.0). Next, eluates were obtained by flowing 2 column volumes of the elution solution (0.2M citric acid) (pH 3.0), neutralized using 1M Tris, and concentrations were checked by measuring absorbance at 280 nm. The GE PD-10 column was equilibrated with 25 ml of physiological saline and then centrifuged (1000 g, 2 minutes). Then, 2.5 ml of the antibody eluate obtained from the protein A column was added into the column and centrifuged (1000 g, 2 minutes) to exchange the antibody solution with saline. The antibody concentration was then measured using absorbance at 280 nm, aliquoted and stored at −80° C.

2-3. Sequence Analysis of Monoclonal Antibodies Against MRS and Cloning

Sequences of 1E8 antibody and 8A12 antibody obtained in the above examples were analyzed by YBIO Inc. and AbClon Inc., Korea. RNA was extracted from the hybridoma cells obtained in Example 1 to synthesize cDNA. Next, PCR was performed using VL, CL, VH, or CH specific primers. PCR products of expected size were separated on the agarose gel and purified to check the sequence through sequencing analysis. CDR domains were identified by Kabat numbering, and Fab was synthesized from the identified sequences, and it was proven that the antibody had high binding ability to MRS by using ELISA method.

In addition, it was confirmed that the sequences of the antibodies were in agreement with the results of mass spectrometry analysis of the protein sequences of the antibodies obtained through the ascites purification after injecting the hybridoma cells into the mouse peritoneum.

The obtained 1E8 Fab sequences and 8A12 Fab sequences were cloned into mouse IgG heavy chain vector (pFUSE-mIgG2a-Fc, InvivoGen) and mouse light chain sequence vector (pFUSE2-CLIg-mK, InvivoGen). Next, those vectors were subjected to co-transfection into freestyle 293F cells using PEI (Polysciences, 23966-2) to have the light and heavy chains of each antibody express simultaneously. Co-transfected 293F cells were incubated at 37° C., 8% $CO_2$ for 7 days. Then, cells were centrifuged to obtain supernatant, and pH of the supernatant was adjusted to 7.6 using a prepared 20× binding solution (1M potassium phosphate dibasic, pH 9.0). Then, the supernatant was filtered with a 0.22 μm filter to obtain a neutralized antibody culture solution. Antibodies were collected from the antibody culture solution by the method described in Example 2-2. It was confirmed that thus obtained whole antibody of 1E8 IgG consists of a light chain having the amino acid sequence of SEQ ID NO:35 and a heavy chain having the amino acid sequence of SEQ ID NO:36, and the whole antibody of 8A12 IgG consists of a light chain having the amino acid sequence of SEQ ID NO:37 and a heavy chain having the amino acid sequence of SEQ ID NO:38.

Example 3

Binding Specificity of Antibodies Against MRS 3-1. Western Blot Experiment Using Anti-MRS Antibody In order to confirm MRS binding ability of 1E8 and 8A12 antibody obtained in the above Examples, experiments were performed as follows.

H460 cells were cultured according to the method described in the above examples and treated with si-MRS for 72 hours. H460 cells were then harvested, lysed, and subjected to western blot. 1E8 antibody and 8A12 antibody were diluted 1:5000 (0.2 μg/ml) and used as primary antibodies. Commercially available anti-MRS antibody (Abcam, Ab50793) was used as well. Tubulin was used as a control.

As a result, as shown in FIG. 1, both 1E8 antibody and 8A12 antibody were found to detect MRS weakly in the si-MRS treated group compared to the untreated group. From this, it was proven that 1E8 antibody and 8A12 antibody binds to MRS specifically. In addition, it was also found that 1E8 antibody and 8A12 antibody were more sensitive than the commercially available anti-MRS antibody at the same concentration.

3-2. ELISA Experiments Using Anti-MRS Antibody

In order to examine the cross-reactivity of 1E8 and 8A12 antibodies obtained in the above examples with other aminoacyl-tRNA synthetase (ARS) proteins, experiments were performed as follows.

Each well of 96 well plates (Corning 3690 flat bottom, 96-well half-area plates) was coated with different kinds of ARS proteins (His-MRS, MRS full, DX2 tag free, 34S-DX2, 34S-AIMP2, His-CRS, His-AIMP1, His-GRS, His-WRS, His-KRS) at the concentration of 1 μg/ml. 1E8 and 8A12 antibodies at a concentration of 500 ng/ml were added onto the 96 well plates coated with ARS proteins and allowed to react for 1 hour. Thereafter, HRP-conjugated anti-mouse IgG secondary antibody was added and reacted for 1 hour. ELISA was performed and absorbance was measured at 450 nm. TMB (3,3',5,5'-tetramethylbenzidine) was used as substrate.

Figure 2A:
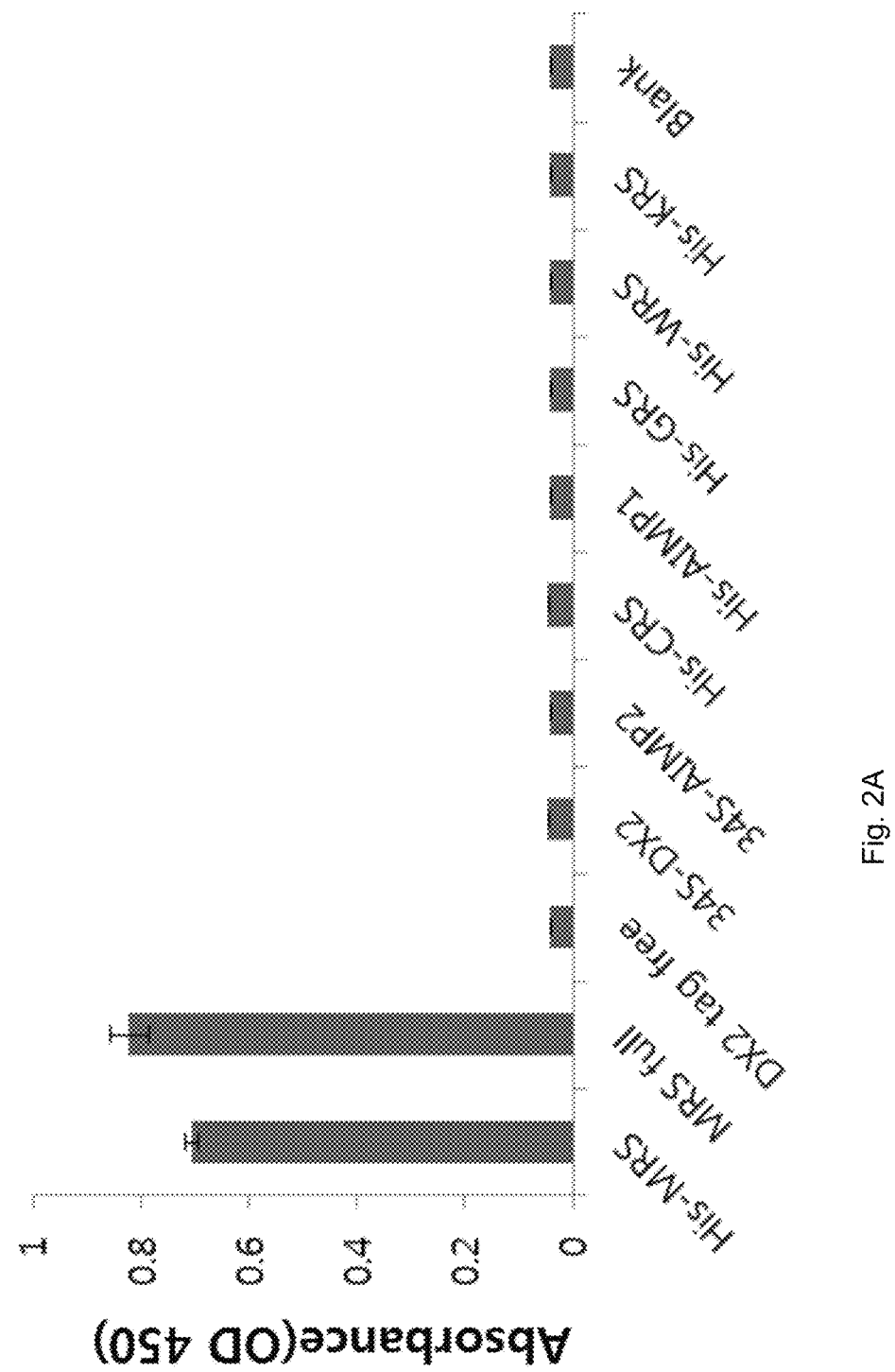
FIGS. 2A and 2B are graphs showing the results of ELISA to confirm the cross-reactivity of anti-MRS antibodies (1E8, 8A12) to ARS (aminoacyl-tRNA synthetase) protein.
Figure 2B:
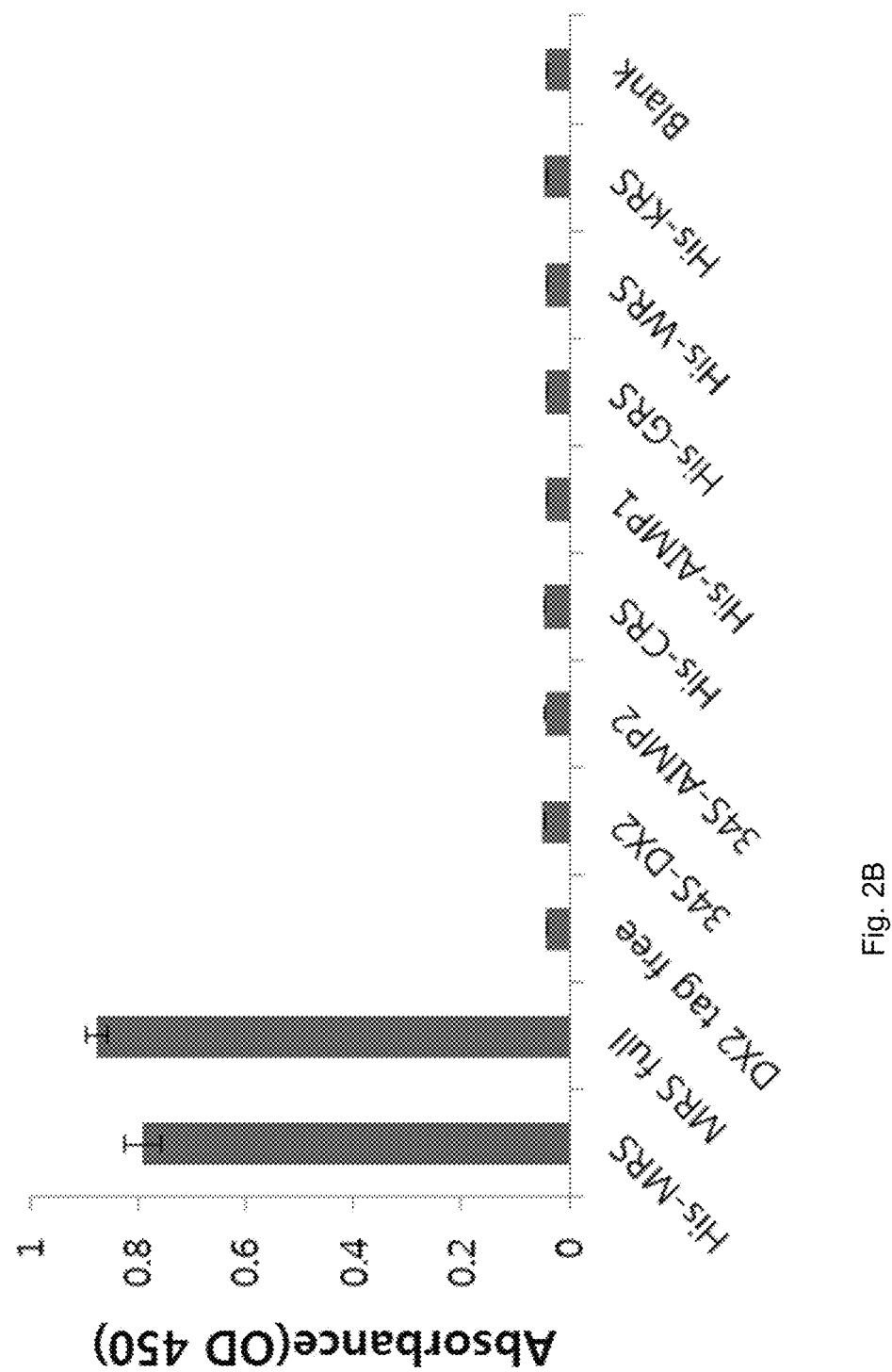
Figure 3A:
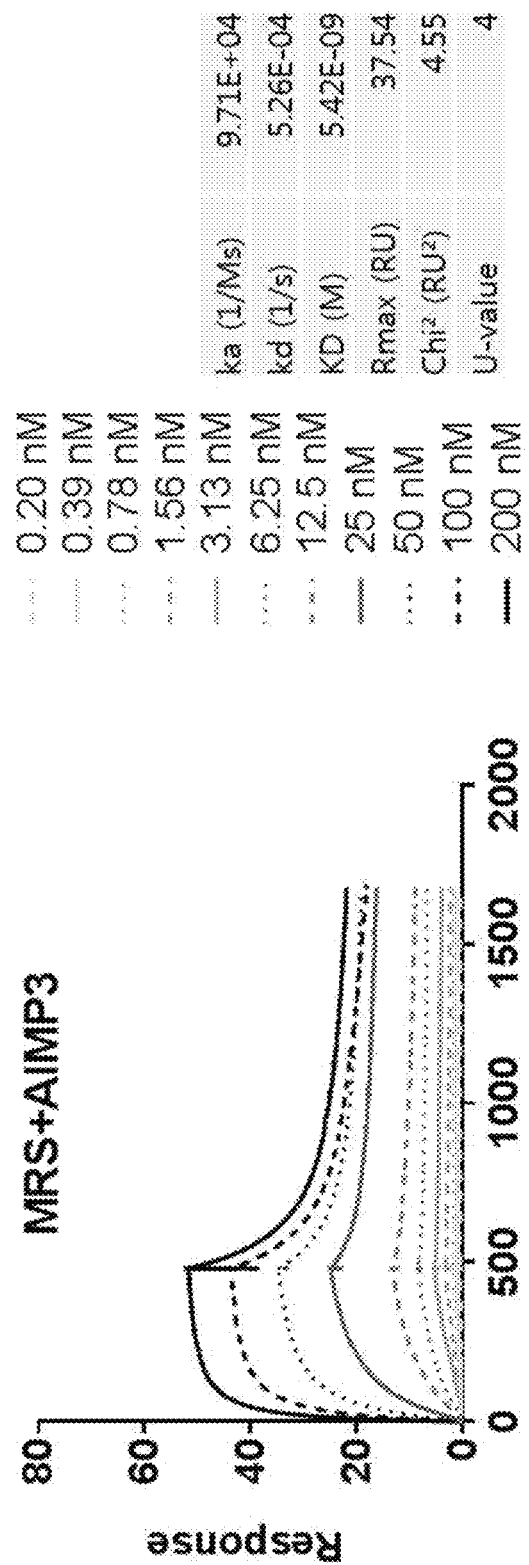
FIGS. 3A and 3B shows the results of the surface plasmon resonance (SPR) experiments to confirm the antibody affinity of anti-MRS antibody (1E8) for MRS+AIMP3 protein.
Figure 3B:
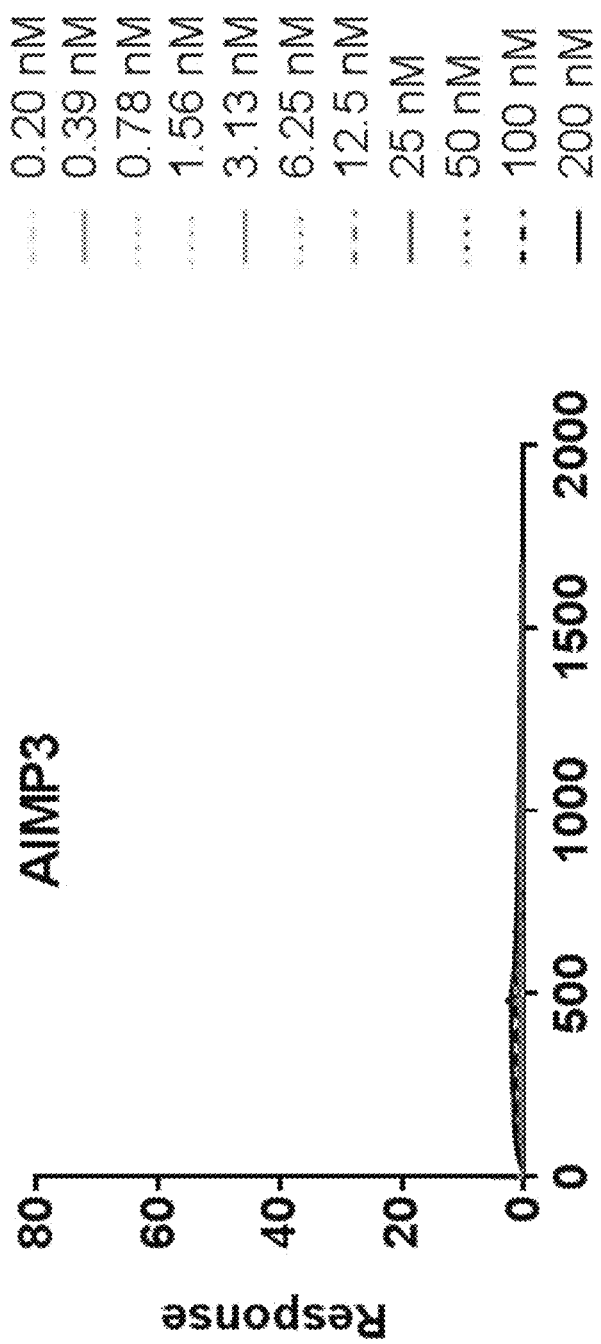

As a result, as shown in FIG. 2A and FIG. 2B, both 1E8 and 8A12 antibody were shown to react and bind only to MRS, not to other ARS proteins and AIMP proteins. Based on this, it was found that 1E8 and 8A12 antibody have no cross-reactivity with other ARS proteins and AIMP proteins, and detect only MRS.

3-3. Examination of Antibody Affinity Using Surface Plasmon Resonance

In order to confirm the affinity of the antibodies purified in Example 2, experiments were carried out as follows.

Surface plasmon resonance (SPR) experiments were carried out using 1E8 and 8A12 antibodies and MRS+AIMP3 protein obtained in Example 1.

CM5 chips were coated with MRS+AIMP3 or AIMP3 proteins and 1E8 or 8A12 antibodies were flowed at various concentrations to measure the degree of binding reaction with the proteins. Samples or buffers were injected for 8 minutes at a flow rate of 30 μl/min and washed for 20 minutes.

Figure 4A:
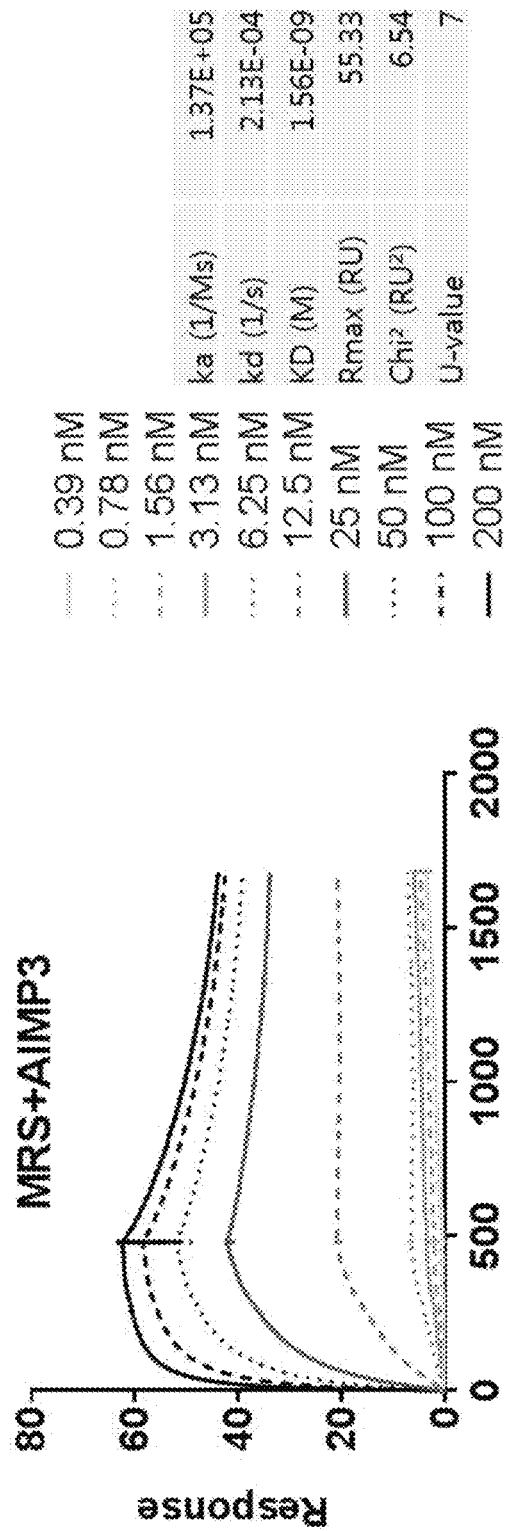
FIGS. 4A and 4B shows the results of the surface plasmon resonance (SPR) experiments to confirm the antibody affinity of anti-MRS antibody (8A12) for MRS+AIMP3 protein.
Figure 4B:
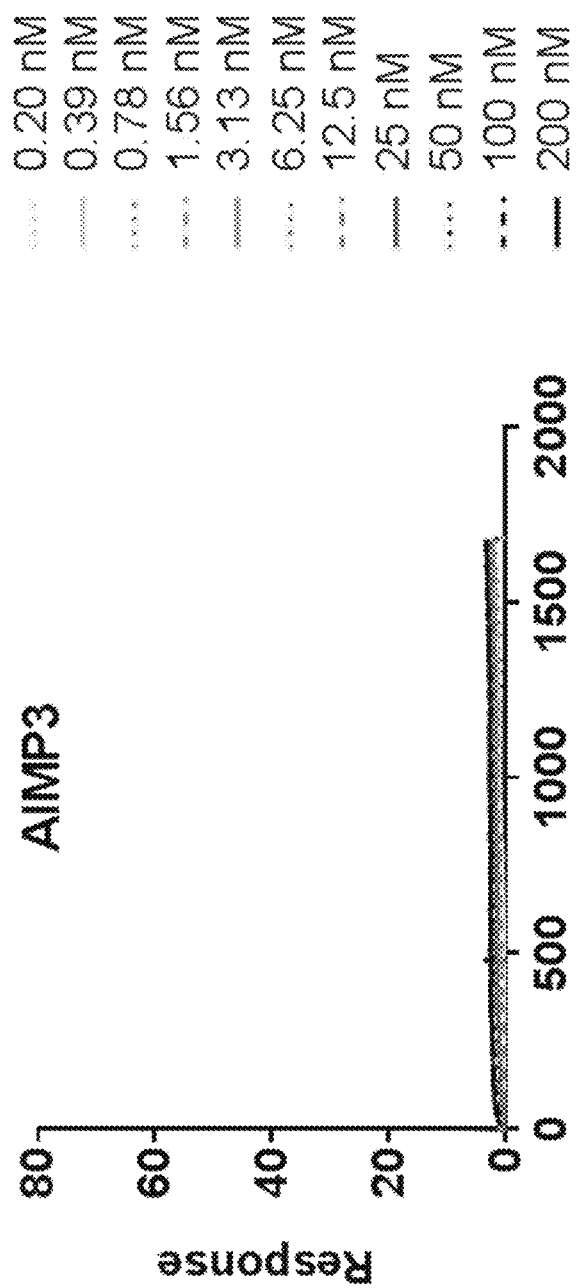

As a result, as shown in FIGS. 3A, 3B, 4A, and 4B, it was confirmed that 1E8 and 8A12 antibodies bind to MRS+AIMP3 proteins but not to the same AIMP3 proteins. In addition, it was measured that 1E8 antibody had a KD value of 5.42 nM for MRS (FIGS. 3A and 3B), and 8A12 antibody had a KD value of 1.56 nM for MRS (FIGS. 4A and 4B).

Example 4

Measurement of Antibody Reactivity Against MRS

In order to check the immune activity of 1E8 antibody and 8A12 antibody obtained in Example 2, experiments were carried out as follows.

Cultured Panc-1 cells were treated with 20 mM EDTA to detach cells, and then centrifuged. Then, the cover glass was put in a 6 well plate, 1 ml of culture medium was added, and cells at $1.0 \times 10^6$ cells/ml were added and cultured at 37° C. Then, the culture medium was removed, and cells were fixed with methanol, followed by 0.2% PBST (PBS+tween 20) treatment and blocking with 2% goat serum (Abchem) for 1 hour. Subsequently, 1E8 and 8A12 antibodies were diluted at a ratio of 1:200 and reacted overnight at 4° C. Mouse IgG alexa 488 (Abchem) was diluted 1:200 with as the secondary antibody and reacted for 1 hour at room temperature. After washing with 0.2% PBST, cells were stained with DAPI (molecular probes) and observed with a fluorescence microscope (Nikon).

Figure 5:
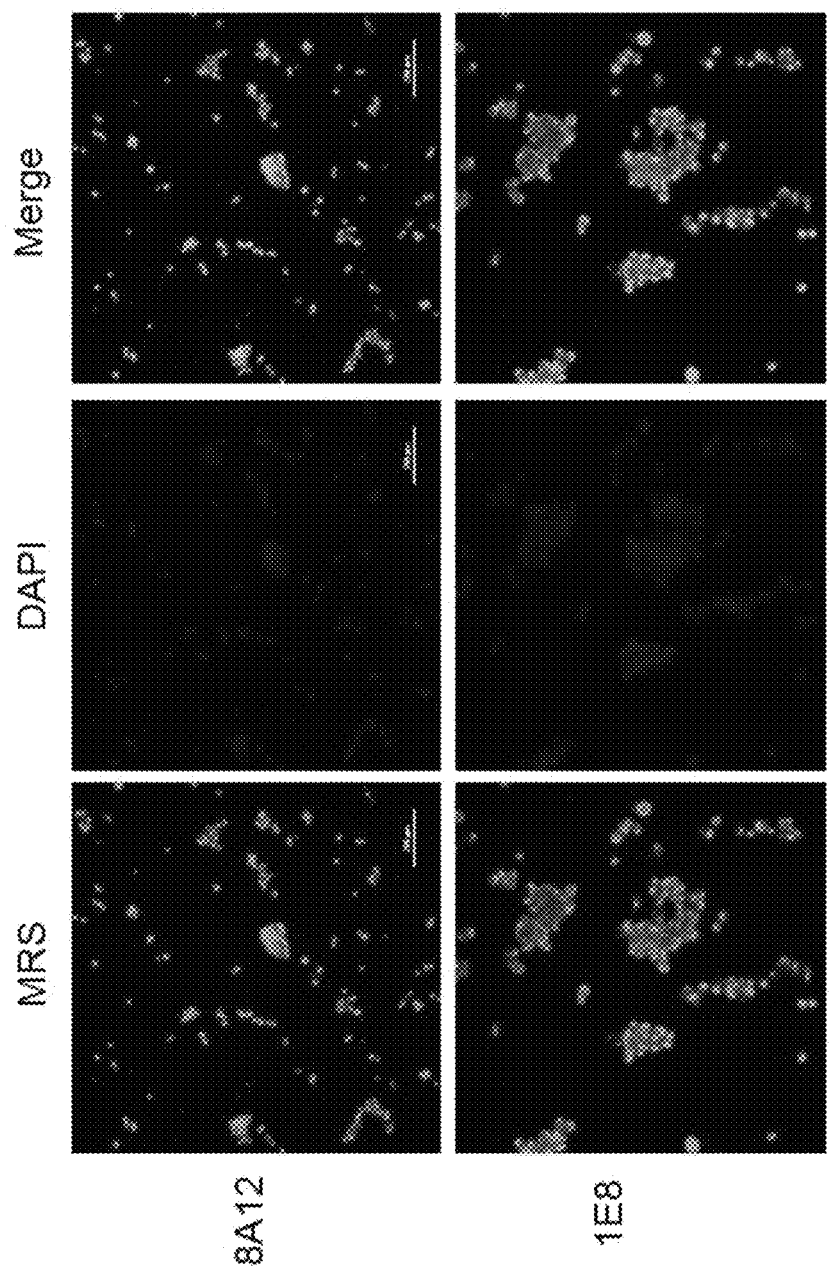
FIG. 5 is a set of images showing the results of an immunofluorescence labeling experiments to confirm the binding to Panc-1 cells using anti-MRS antibodies (1E8 and 8A12) (green: MRS, blue: nucleus).

As a result, as shown in FIG. 5, it was confirmed that 1E8 antibody and 8A12 antibody obtained in Example 2 bind to the surface of Panc-1 cells.

Example 5

Identification of Binding Site of Anti-MRS Antibody

In order to identify the domains of 1E8 antibody and 8A12 antibody obtained in Example 2, the following experiments were performed.

Six fragments of different lengths and positions were prepared based on the GST, catalytic domain, and tRNA binging domains of the MRS protein, and MRS protein and each of the MRS fragments were cloned into pcDNA3 vector (EV). The position of each MRS fragment is shown in Table 1 below. At this time, since Myc protein is linked to the N-terminus of MRS protein, Myc protein was used as a control.

Then, 2 μg of the cloned vector DNA were transfected into H460 cells using Turbofect (Thermo) according to the manufacturer's instructions. After 24 hours, cells were harvested and subjected to western blot. 1E8 antibody and 8A12 antibody were diluted 1:5000 (0.2 μg/mL) as the primary antibody.

Figure 6A:
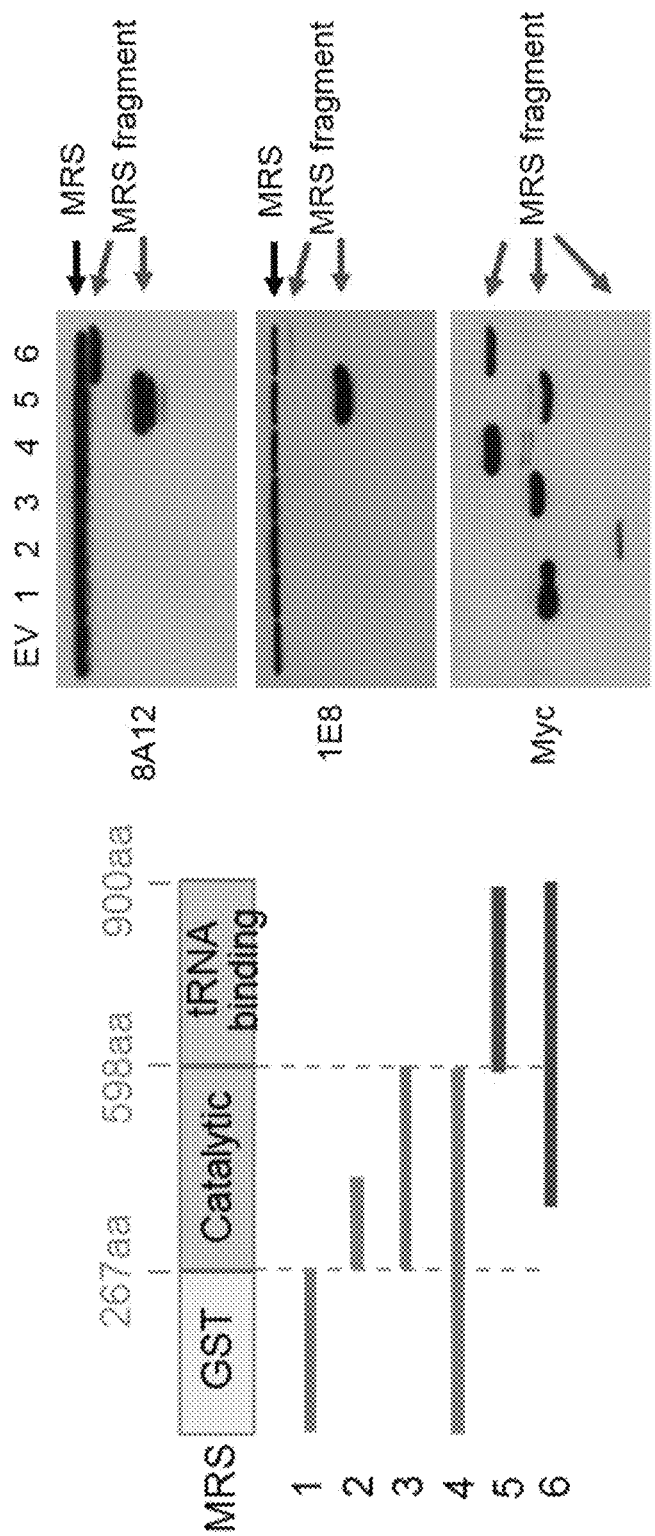
FIG. 6A shows the results of western blot experiments by extracting proteins after transfection of H460 cells with MRS or 6 MRS fragments having different sequences.

As a result, as shown in FIG. 6A, both 1E8 antibody and 8A12 antibody were found to recognize MRS fragments 5 and 6.

Through this observation, it was confirmed that antibodies bind to 598~900 aa.

Based on this results, four fragments of different lengths and positions were prepared from the 598~900 aa portion of MRS protein, and each fragment was cloned into pcDNA3 vector (EV). Then, western blot was performed in the same manner as described above.

Figure 6B:
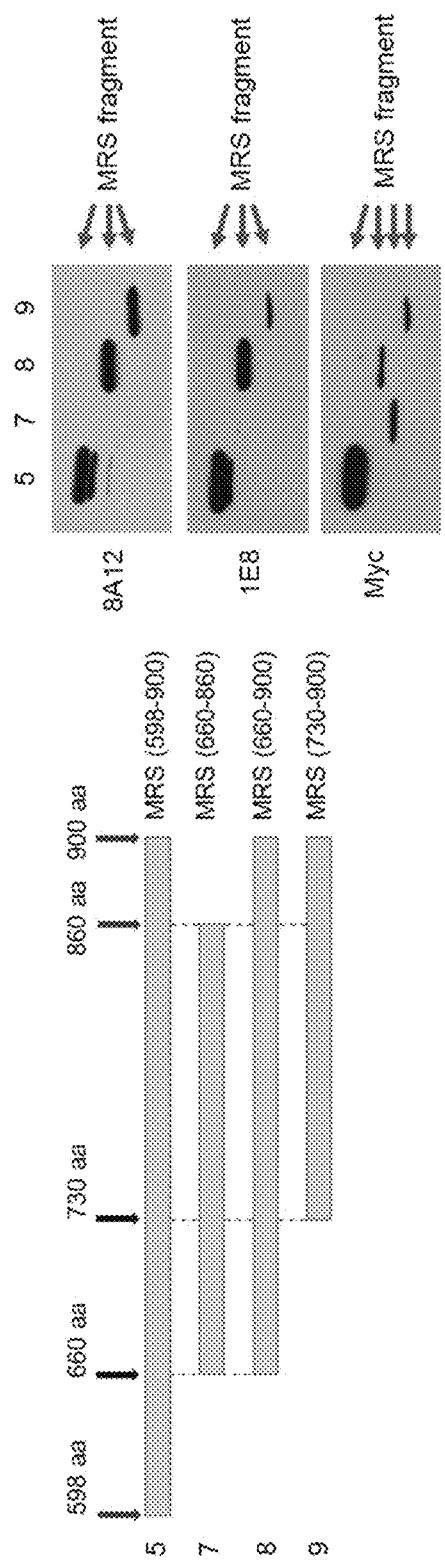
FIG. 6B shows the results of western blot experiments by extracting proteins after transfection of H460 cells with MRS or 4 MRS fragments having different sequences.

As a result, as shown in FIG. 6B, both 1E8 antibody and 8A12 antibody recognized fragments 5, 8, and 9, but it turned out that they did not recognize fragment 7.

From this finding, it was confirmed that both antibodies bind to the 861~900 aa position of the MRS protein.

TABLE 1

| MRS fragment | Position | Sequence | Sequence number |
|---|---|---|---|
| 1 | 1~266 aa | MRLFVSDGVPGCLPVLAAAGRARGRAEVLISTVGP EDCVVPFLTRPKVPVLQLDSGNYLFSTSAICRYFF LLSGWEQDDLTNQWLEWEATELQPALSAALYYLVV QGKKGEDVLGSVRRALTHIDHSLSRQNCPFLAGET ESLADIVLWGALYPLLQDPAYLPEELSALHSWFQT LSTQEPCQRAAETVLKQQGVLALRPYLQKQPQPSP AEGRAVTNEPEEEELATLSEEEIAMAVTAWEKGLE SLPPLRPQQNPVLPVAGERNV | 40 |
| 2 | 267~417 aa | LITSALPYVNNVPHLGNIIGCLVSADVFARYSRLR QWNTLYLCGTDEYGTATETKALEEGLTPQEICDKY HIIHADIYRWFNISFDIFGRTTTPQQTKITQDIFQ QLLKRGFVLQDTVEQLRCEHCARFLADRFVEGVCP FCGYEEARGDQ | 41 |
| 3 | 267~597 aa | LITSALPYVNNVPHLGNIIGCVLSADVFARYSRLR QWNTLYLCGTDEYGTATETKALEEGLTPQEICDKY HIIHADIYRWFNISFDIFGRTTTPQQTKITQDIFQ QLLKRGFVLQDTVEQLRCEHCARFLADRFVEGVCP FCGYEEARGDQCDKCGLKINAVELKKPQCKVCRSC PVVQSSQHLFLDLPKLEKRLEEWLGRTLPGSDWTP NAQFITRSWLRDGLKPRCITRDLKWGTPVPLEGFE DKVFYVWFDATIGYLSITANYTDQWERWWKNPEQV DLYQFMAKDNVPFHSLVFPCSALGAEDNYTLVSHL IATEYLNYEDGKFSKS | 42 |
| 4 | 1~597 aa | MRLFVSDGVPGCLPVLAAAGRARGRAEVLISTVGP EDCVVPFLTRPKVPVLQLDSGNYLFSTSAICRYFF LLSGWEQDDLTNQWLEWEATELQPALSAALYYLVV QGKKGEDVLGSVRRALTHIDHSLSRQNCPFLAGET ESLADIVLWGALYPLLQDPAYLPEELSALHSWFQT LSTQEPCQRAAETVLKQQGVLALRPYLQKQPQPSP AEGRAVTNEPEEEELATLSEEEIAMAVTAWEKGLE SLPPLRPQQNPVLPVAGERNVLITSALPYVNNVPH LGNIIGCVLSADVFARYSRLRQWNTLYLCGTDEYG TATETKALEEGLTPQEICDKYHIIHADIYWRFNIS FDIFGRTTTPQQTKITQDIFQQLLKRGFVLQDTVE QLRCEHCARFLADRFVEGVCPFCGYEEARGDQCDK CGKLINAVELKKPQCKVCRSCPVVQSSQHLFLDLP KLEKRLEEWLGRTLPGSDWTPNAQFITRSWLRDGL KPRCITRDLKWGTPVPLEGFEDKVFYVWFDATIGY LSITANYTDQWERWWKNPEQVDLYQFMAKDNVPFH SLVFPCSALGAEDNYTLVSHLIATEYLNYEDGKFS KS | 43 |
| 5 | 598~900 aa | RGVGVFGDMAQDTGIPADIWRFYLLYIRPEGQDSA FSWTDLLLKNNSELLNNLGNFINRAGMFVSKFFGG YVPEMVLTPDDQRLLAHVTLELQHYHQLLEKVRIR DALRSILTISRHGNQYIQVNEPWKRIKGSEADRQR AGTVTGLAVNIAALLSVMLQPYMPTVSATIQAQLQ LPPPACSILLTNFLCTLPAGHQIGTVSPLFQKLEN DQIESLRQRFGGGQAKTSPKPAVVETVTTAKPQQI QALMDEVTKQGNIVRELKAQKADKNEVAAEVAKLL DLKKQLAVAEGKPPEAPKGKKKK | 44 |
| 6 | 298~900 aa | SRLRQWNTLYLCGTDEYGTATETKALEEGLTPQEI CDKYHIIHADIYRWFNISFDIFGRTTTPQQTKITQ DIFQQLLKRGFVLQDTVEQLRCEHCARFLADRFVE | 45 |

TABLE 1-continued

| MRS fragment | Position | Sequence | Sequence number |
|---|---|---|---|
| | | GVCPFCGYEEARGDQCDKCGLKINAVELKKPQCKV CRSCPVVQSSQHLFLDLPKLEKRLEEWLGRTLPGS DWTPNAQFITRSWLRDGLKPRCITRDLKWGTPVPL EGFEDKVFYVWFDATIGYLSITANYTDQWERWWKN PEQVDLYQFMAKDNVPFHSLVFPCSALGAEDNYTL VSHLIATEYLNYEDGKFSKSRGVGVFGDMAQDTGI PADIWRFYLLYIRPEGQDSAFSWTDLLLKNNSELL NNLGNFINRAGMFVSKFFGGYVPEMVLTPDDQRLL AHVTLELQHYHQLLEKVRIRDALRSILTISRHGNQ YIQVNEPWKRIKGSEADRQRAGTVTGLAVNIAALL SVMLQPYMPTVSATIQAQLQLPPPACSILLTNFLC TLPAGHQIGTVSPLFQKLENDQIESLRQRFGGGQA KTSPKPAVVETVTTAKPQQIQALMDEVTKQGNIVR ELKAQKADKNEVAAEVAKLLDLKKQLAVAEGKPPE ARKGKKKK | |
| 7 | 660~860 aa | FVSKFFGGYVPEMVLTPDDQRLLAHVTLELQHYHQ LLEKVRIRDALRSILTISRHGNQYIQVNEPWKRIK GSEADRQRAGTVTGLAVNIAALLSVMLQPYMPTVS ATIQAQLQLPPPACSILLTNFLCTLPAGHQIGTVS PLFQKLENDQIESLRQRFGGGQAKTSPKPAVVETV TTAKPQQIQALMDEVTKQGNIVRELK | 46 |
| 8 | 660~900 aa | FVSKFFGGYVPEMVLTPDDQRLLAHVTLELQHYHQ LLEKVRIRDALRSILTISRHGNQYIQVNEPWKRIK GSEADRQRAGTVTGLAVNIAALLSVMLQPYMPTVS ATIQAQLQLPPPACSILLTNFLCTLPAGHQIGTVS PLFQKLENDQIESLRQRFGGGQAKTSPKPAVVETV TTAKPQQIQALMDEVTKQGNIVRELKAQKADKNEV AAEVAKLLDLKKQLAVAEGKPPEAPKGKKKK | 47 |
| 9 | 730~900 aa | GSEADRQRAGTVTGLAVNIAALLSVMLQPYMPTVS ATIQAQLQLPPPACSILLTNFLCTLPAGHQIGTVS PLFQKLENDQIESLRQRFGGGQAKTSPKPAVVETV TTAKPQQIQALMDEVTKQGNIVRELKAQKADKNEV AAEVAKLLDLKKQLAVAEGKPPEAPKGKKKK | 48 |

INDUSTRIAL APPLICABILITY

As described above, the antibody or fragment thereof of the present invention specifically binds to human-derived MRS, and has no cross-reactivity with other proteins including the same ARS family, thus making it possible to detect MRS. Can be used.

---

What is claimed is:

1. An antibody or an antigen-binding fragment thereof which binds specifically to a peptide fragment consisting of the 861$^{st}$ to 900$^{th}$ amino acid residues of human-derived methionyl-tRNA synthetase (MRS) protein as set forth in SEQ ID NO:1,
wherein the antibody or the fragment comprises:
a light chain variable region (VL) comprising a light chain complementarity determining region 1 (CDR1) comprising an amino acid sequence as set forth in SEQ ID NO:3 or SEQ ID NO:15; a light chain complementarity determining region 2 (CDR2) comprising an amino acid sequence as set forth in SEQ ID NO:5 or SEQ ID NO:17; and a light chain complementarity determining region 3 (CDR3) comprising an amino acid sequence as set forth in SEQ ID NO:7 or SEQ ID NO:19; and
a heavy chain variable region (VH) comprising a heavy chain complementarity determining region 1 (CDR1) comprising an amino acid sequence as set forth in SEQ ID NO:9 or SEQ ID NO:21; a heavy chain complementarity determining region 2 (CDR2) comprising an amino acid sequence as set forth in SEQ ID NO:11 or SEQ ID NO:23; and a heavy chain complementarity determining region 3 (CDR3) comprising an amino acid sequence as set forth in SEQ ID NO:13 or SEQ ID NO:25.

2. The antibody or the fragment thereof of claim 1, wherein the antibody or the fragment comprises a heavy chain variable region and a light chain variable region selected from the group consisting of:
the light chain variable region (VL) comprising the light chain complementarity determining region 1 (CDR1) comprising the amino acid sequence as set forth in SEQ ID NO:3, the light chain complementarity determining region 2 (CDR2) comprising the amino acid sequence as set forth in SEQ ID NO:5, and the light chain complementarity determining region 3 (CDR3) comprising the amino acid sequence as set forth in SEQ ID NO:7, and the heavy chain variable region (VH) comprising the heavy chain complementarity determining region 1 (CDR1) comprising an amino acid sequence as set forth in SEQ ID NO:9, the heavy chain complementarity determining region 2 (CDR2) comprising the amino acid sequence as set forth in SEQ ID NO:11, and the heavy chain complementarity determining region 3 (CDR3) comprising the amino acid sequence as set forth in SEQ ID NO:13; and
the light chain variable region (VL) comprising the light chain complementarity determining region 1 (CDR1) comprising the amino acid sequence as set forth in SEQ ID NO:15, the light chain complementarity determining region 2 (CDR2) comprising the amino acid sequence as set forth in SEQ ID NO:17, and the light chain complementarity determining region 3 (CDR3) comprising the amino acid sequence as set forth in SEQ ID NO:19, and the heavy chain variable region (VH) comprising the heavy chain complementarity determining region 1 (CDR1) comprising an amino acid sequence as set forth in SEQ ID NO:21, the heavy chain complementarity determining region 2 (CDR2) comprising the amino acid sequence as set forth in SEQ ID NO:23, and the heavy chain complementarity determining region 3 (CDR3) comprising the amino acid sequence as set forth in SEQ ID NO:25.

3. The antibody or the fragment thereof of claim 1, wherein the light chain variable region comprises a amino acid sequence as set forth in SEQ ID NO:27 or SEQ ID NO:31 and the heavy chain variable region comprises a amino acid sequence as set forth in SEQ ID NO:29 or SEQ ID NO:33.

4. The antibody or the fragment thereof of claim 1, wherein the antibody is selected from the group consisting of IgG, IgA, IgM, IgE and IgD, and the fragment thereof is selected from the group consisting of diabody, Fab, Fab', F(ab)2, F(ab')2, Fv and scFv.

* * * * *

SEQUENCE LISTING

<160> NUMBER OF SEQ ID NOS: 49

<210> SEQ ID NO 1
<211> LENGTH: 900
<212> TYPE: PRT
<213> ORGANISM: Homo sapiens
<220> FEATURE:
<223> OTHER INFORMATION: MRS protein (NP_004981.2)

<400> SEQUENCE: 1

Met Arg Leu Phe Val Ser Asp Gly Val Pro Gly Cys Leu Pro Val Leu
1               5                   10                  15

Ala Ala Ala Gly Arg Ala Arg Gly Arg Ala Glu Val Leu Ile Ser Thr
            20                  25                  30

Val Gly Pro Glu Asp Cys Val Val Pro Phe Leu Thr Arg Pro Lys Val
            35                  40                  45

Pro Val Leu Gln Leu Asp Ser Gly Asn Tyr Leu Phe Ser Thr Ser Ala
            50                  55                  60

Ile Cys Arg Tyr Phe Phe Leu Leu Ser Gly Trp Glu Gln Asp Asp Leu

```
            65                  70                  75                  80
Thr Asn Gln Trp Leu Glu Trp Glu Ala Thr Glu Leu Gln Pro Ala Leu
                85                  90                  95

Ser Ala Ala Leu Tyr Tyr Leu Val Val Gln Gly Lys Lys Gly Glu Asp
            100                 105                 110

Val Leu Gly Ser Val Arg Arg Ala Leu Thr His Ile Asp His Ser Leu
            115                 120                 125

Ser Arg Gln Asn Cys Pro Phe Leu Ala Gly Glu Thr Glu Ser Leu Ala
        130                 135                 140

Asp Ile Val Leu Trp Gly Ala Leu Tyr Pro Leu Leu Gln Asp Pro Ala
145                 150                 155                 160

Tyr Leu Pro Glu Glu Leu Ser Ala Leu His Ser Trp Phe Gln Thr Leu
                165                 170                 175

Ser Thr Gln Glu Pro Cys Gln Arg Ala Ala Glu Thr Val Leu Lys Gln
            180                 185                 190

Gln Gly Val Leu Ala Leu Arg Pro Tyr Leu Gln Lys Gln Pro Gln Pro
            195                 200                 205

Ser Pro Ala Glu Gly Arg Ala Val Thr Asn Glu Pro Glu Glu Glu Glu
        210                 215                 220

Leu Ala Thr Leu Ser Glu Glu Ile Ala Met Ala Val Thr Ala Trp
225                 230                 235                 240

Glu Lys Gly Leu Glu Ser Leu Pro Pro Leu Arg Pro Gln Gln Asn Pro
                245                 250                 255

Val Leu Pro Val Ala Gly Glu Arg Asn Val Leu Ile Thr Ser Ala Leu
            260                 265                 270

Pro Tyr Val Asn Asn Val Pro His Leu Gly Asn Ile Ile Gly Cys Val
            275                 280                 285

Leu Ser Ala Asp Val Phe Ala Arg Tyr Ser Arg Leu Arg Gln Trp Asn
        290                 295                 300

Thr Leu Tyr Leu Cys Gly Thr Asp Glu Tyr Gly Thr Ala Thr Glu Thr
305                 310                 315                 320

Lys Ala Leu Glu Glu Gly Leu Thr Pro Gln Glu Ile Cys Asp Lys Tyr
                325                 330                 335

His Ile Ile His Ala Asp Ile Tyr Arg Trp Phe Asn Ile Ser Phe Asp
            340                 345                 350

Ile Phe Gly Arg Thr Thr Thr Pro Gln Gln Thr Lys Ile Thr Gln Asp
            355                 360                 365

Ile Phe Gln Gln Leu Leu Lys Arg Gly Phe Val Leu Gln Asp Thr Val
        370                 375                 380

Glu Gln Leu Arg Cys Glu His Cys Ala Arg Phe Leu Ala Asp Arg Phe
385                 390                 395                 400

Val Glu Gly Val Cys Pro Phe Cys Gly Tyr Glu Glu Ala Arg Gly Asp
                405                 410                 415

Gln Cys Asp Lys Cys Gly Lys Leu Ile Asn Ala Val Glu Leu Lys Lys
            420                 425                 430

Pro Gln Cys Lys Val Cys Arg Ser Cys Pro Val Val Gln Ser Ser Gln
            435                 440                 445

His Leu Phe Leu Asp Leu Pro Lys Leu Glu Lys Arg Leu Glu Glu Trp
        450                 455                 460

Leu Gly Arg Thr Leu Pro Gly Ser Asp Trp Thr Pro Asn Ala Gln Phe
465                 470                 475                 480

Ile Thr Arg Ser Trp Leu Arg Asp Gly Leu Lys Pro Arg Cys Ile Thr
                485                 490                 495
```

```
Arg Asp Leu Lys Trp Gly Thr Pro Val Pro Leu Glu Gly Phe Glu Asp
            500                 505                 510
Lys Val Phe Tyr Val Trp Phe Asp Ala Thr Ile Gly Tyr Leu Ser Ile
            515                 520                 525
Thr Ala Asn Tyr Thr Asp Gln Trp Glu Arg Trp Trp Lys Asn Pro Glu
            530                 535                 540
Gln Val Asp Leu Tyr Gln Phe Met Ala Lys Asp Asn Val Pro Phe His
545                 550                 555                 560
Ser Leu Val Phe Pro Cys Ser Ala Leu Gly Ala Glu Asp Asn Tyr Thr
                565                 570                 575
Leu Val Ser His Leu Ile Ala Thr Glu Tyr Leu Asn Tyr Glu Asp Gly
            580                 585                 590
Lys Phe Ser Lys Ser Arg Gly Val Gly Val Phe Gly Asp Met Ala Gln
            595                 600                 605
Asp Thr Gly Ile Pro Ala Asp Ile Trp Arg Phe Tyr Leu Leu Tyr Ile
            610                 615                 620
Arg Pro Glu Gly Gln Asp Ser Ala Phe Ser Trp Thr Asp Leu Leu Leu
625                 630                 635                 640
Lys Asn Asn Ser Glu Leu Leu Asn Asn Leu Gly Asn Phe Ile Asn Arg
                645                 650                 655
Ala Gly Met Phe Val Ser Lys Phe Phe Gly Gly Tyr Val Pro Glu Met
                660                 665                 670
Val Leu Thr Pro Asp Asp Gln Arg Leu Leu Ala His Val Thr Leu Glu
            675                 680                 685
Leu Gln His Tyr His Gln Leu Leu Glu Lys Val Arg Ile Arg Asp Ala
            690                 695                 700
Leu Arg Ser Ile Leu Thr Ile Ser Arg His Gly Asn Gln Tyr Ile Gln
705                 710                 715                 720
Val Asn Glu Pro Trp Lys Arg Ile Lys Gly Ser Glu Ala Asp Arg Gln
                725                 730                 735
Arg Ala Gly Thr Val Thr Gly Leu Ala Val Asn Ile Ala Ala Leu Leu
            740                 745                 750
Ser Val Met Leu Gln Pro Tyr Met Pro Thr Val Ser Ala Thr Ile Gln
            755                 760                 765
Ala Gln Leu Gln Leu Pro Pro Pro Ala Cys Ser Ile Leu Leu Thr Asn
            770                 775                 780
Phe Leu Cys Thr Leu Pro Ala Gly His Gln Ile Gly Thr Val Ser Pro
785                 790                 795                 800
Leu Phe Gln Lys Leu Glu Asn Asp Gln Ile Glu Ser Leu Arg Gln Arg
                805                 810                 815
Phe Gly Gly Gly Gln Ala Lys Thr Ser Pro Lys Pro Ala Val Val Glu
                820                 825                 830
Thr Val Thr Thr Ala Lys Pro Gln Gln Ile Gln Ala Leu Met Asp Glu
            835                 840                 845
Val Thr Lys Gln Gly Asn Ile Val Arg Glu Leu Lys Ala Gln Lys Ala
            850                 855                 860
Asp Lys Asn Glu Val Ala Ala Glu Val Ala Lys Leu Leu Asp Leu Lys
865                 870                 875                 880
Lys Gln Leu Ala Val Ala Glu Gly Lys Pro Pro Glu Ala Pro Lys Gly
                885                 890                 895
Lys Lys Lys Lys
            900
```

<210> SEQ ID NO 2
<211> LENGTH: 2703
<212> TYPE: DNA
<213> ORGANISM: Homo sapiens
<220> FEATURE:
<223> OTHER INFORMATION: MRS mRNA (NM_004990.3)

<400> SEQUENCE: 2

```
atgagactgt tcgtgagtga tggcgtcccg ggttgcttgc cggtgctggc cgccgccggg      60
agagcccggg gcagagcaga ggtgctcatc agcactgtag gcccggaaga ttgtgtggtc     120
ccgttcctga cccggcctaa ggtccctgtc ttgcagctgg atagcggcaa ctacctcttc     180
tccactagtg caatctgccg atatttttttt tgttatctg gctgggagca agatgacctc     240
actaaccagt ggctggaatg ggaagcgaca gagctgcagc cagctttgtc tgctgccctg     300
tactatttag tggtccaagg caagaagggg gaagatgttc ttggttcagt gcggagagcc     360
ctgactcaca ttgaccacag cttgagtcgt cagaactgtc ctttcctggc tggggagaca     420
gaatctctag ccgacattgt tttgtgggga gccctatacc cattactgca agatcccgcc     480
tacctccctg aggagctgag tgccctgcac agctggttcc agacactgag tacccaggaa     540
ccatgtcagc gagctgcaga gactgtactg aaacagcaag gtgtcctggc tctccggcct     600
tacctccaaa agcagcccca gcccagcccc gctgagggaa gggctgtcac caatgagcct     660
gaggaggagg agctggctac cctatctgag gaggagattc tatggctgt tactgcttgg     720 gagaagggcc tagaaagttt gcccccgctg cggccccagc agaatccagt gttgcctgtg     780
gctggagaaa ggaatgtgct catcaccagt gccctccctt acgtcaacaa tgtccccac     840 cttgggaaca tcattggttg tgtgctcagt gccgatgtct ttgccaggta ctctcgcctc     900
cgccagtgga cacccctcta tctgtgtggg acagatgagt atggtacagc aacagagacc     960
aaggctctgg aggagggact aaccccccag gagatctgcg acaagtacca tcatccat     1020 gctgacatct accgctggtt taacatttcg tttgatattt ttggtcgcac caccactcca    1080
cagcagacca aaatcaccca ggacatttc cagcagttgc tgaaacgagg ttttgtgctg    1140
caagatactg tggagcaact gcgatgtgag cactgtgctc gcttcctggc tgaccgcttc    1200
gtggagggcg tgtgtcccctt ctgtggctat gaggaggctc ggggtgacca gtgtgacaag    1260
tgtggcaagc tcatcaatgc tgtcgagctt aagaagcctc agtgtaaagt ctgccgatca    1320
tgccctgtgg tgcagtcgag ccagcacctg tttctggacc tgcctaagct ggagaagcga    1380
ctggaggagt ggttggggag acattgcct ggcagtgact ggacacccaa tgcccagttt    1440
atcacccgtt cttggcttcg ggatggcctc aagccacgct gcataacccg agacctcaaa    1500
tggggaaccc ctgtacccctt agaaggtttt gaagacaagg tattctatgt ctggtttgat    1560
gccactattg gctatctgtc catcacagcc aactacacag accagtggga gagatggtgg    1620
aagaacccag agcaagtgga cctgtatcag ttcatggcca aagacaatgt tcctttccat    1680
agcttagtct ttccttgctc agccctagga gctgaggata actatacctt ggtcagccac    1740
ctcattgcta cagagtacct gaactatgag gatgggaaat tctctaagag ccgcggtgtg    1800
ggagtgtttg ggacatggc ccaggacacg gggatccctg ctgacatctg gcgcttctat    1860
ctgctgtaca ttcggcctga gggccaggac agtgcttcct cctggacgga cctgctgctg    1920
aagaataatt ctgagctgct taacaacctg gcaacttca tcaacagagc tgggatgttt    1980
gtgtctaagt tctttgggg ctatgtgcct gagatggtgc tcaccctga tgatcagcgc    2040 ctgctggccc atgtcaccct ggagctccag cactatcacc agctacttga gaaggttcgg    2100
```

```
atccgggatg ccttgcgcag tatcctcacc atatctcgac atggcaacca atatattcag    2160
gtgaatgagc cctggaagcg gattaaaggc agtgaggctg acaggcaacg ggcaggaaca    2220
gtgactggct tggcagtgaa tatagctgcc ttgctctctg tcatgcttca gccttacatg    2280
cccacggtta gtgccacaat ccaggcccag ctgcagctcc cacctccagc ctgcagtatc    2340
ctgctgacaa acttcctgtg taccttacca gcaggacacc agattggcac agtcagtccc    2400
ttgttccaaa aattggaaaa tgaccagatt gaaagtttaa ggcagcgctt tggaggggc    2460 caggcaaaaa cgtccccgaa gccagcagtt gtagagactg ttacaacagc caagccacag    2520
cagatacaag cgctgatgga tgaagtgaca aaacaaggaa acattgtccg agaactgaaa    2580
gcacaaaagg cagacaagaa cgaggttgct gcggaggtgg cgaaactctt ggatctaaag    2640
aaacagttgg ctgtagctga ggggaaaccc cctgaagccc taaaggcaa gaagaaaaag     2700 taa                                                                 2703
```

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1E8 VL CDR1

<400> SEQUENCE: 3

Lys Ser Ser Gln Ser Leu Leu Tyr Ser Ser Asn Gln Lys Asn Tyr Leu
1               5                   10                  15

Ala

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 1E8 VL CDR1

<400> SEQUENCE: 4
aagtccagtc agagcctttt atatagtagc aatcaaaaga actacttggc c            51

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1E8 VL CDR2

<400> SEQUENCE: 5

Trp Ala Ser Thr Arg Glu Ser
1               5

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic

```
        oligonucleotide
<220> FEATURE:
<223> OTHER INFORMATION: 1E8 VL CDR2

<400> SEQUENCE: 6
tgggcatcca ctagggaatc t                                           21

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1E8 VL CDR3

<400> SEQUENCE: 7

Gln Gln Tyr Tyr Ser Tyr Pro Thr
1               5

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 1E8 VL CDR3

<400> SEQUENCE: 8
cagcaatatt atagctatcc gacg                                        24

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1E8 VH CDR1

<400> SEQUENCE: 9

Ser Asp Tyr Ala Trp Asn
1               5

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 1E8 VH CDR1

<400> SEQUENCE: 10
agtgattatg cctggaac                                               18

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: 1E8 VH CDR2

<400> SEQUENCE: 11

Tyr Ile Ser Tyr Ser Gly Arg Thr Ser Tyr Lys Ser Ser Leu Lys Ser
1               5                   10                  15

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 1E8 VH CDR2

<400> SEQUENCE: 12
tacataagct acagtggtcg cactagctac aaatcatctc tcaaaagt                48

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1E8 VH CDR3

<400> SEQUENCE: 13

Asp Tyr Gly Asn Phe Val Gly Tyr Phe Asp Val
1               5                   10

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 1E8 VH CDR3

<400> SEQUENCE: 14
gactatggta acttcgtagg ttacttcgat gtc                                33

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8A12 VL CDR1

<400> SEQUENCE: 15

Lys Ala Ser Gln Asp Ile Asn Ser Tyr Leu Ser
1               5                   10

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 8A12 VL CDR1

-continued

<400> SEQUENCE: 16
aaggcgagtc aggacattaa tagctattta agc         33

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8A12 VL CDR2

<400> SEQUENCE: 17

Arg Ala Asn Arg Leu Val Asp
1               5

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 8A12 VL CDR2

<400> SEQUENCE: 18
cgtgcaaaca gattggtaga t         21

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8A12 VL CDR3

<400> SEQUENCE: 19

Leu Gln Tyr Asp Glu Phe Pro Arg Thr
1               5

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 8A12 VL CDR3

<400> SEQUENCE: 20
ctacagtatg atgagtttcc tcggacg         27

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8A12 VH CDR1

<400> SEQUENCE: 21

Ser Glu Tyr Ala Trp Thr
1               5

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 8A12 VH CDR1

<400> SEQUENCE: 22
agtgagtatg cctggacc                                                 18

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8A12 VH CDR2

<400> SEQUENCE: 23

Tyr Ile Asn Tyr Asn Gly Asn Thr Asn Leu Asn Pro Ser Leu Lys Ser
1               5                   10                  15

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 8A12 VH CDR2

<400> SEQUENCE: 24
tacataaact acaatggcaa cactaactta aatccatctc tcaaaagt                 48

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 8A12 VH CDR3

<400> SEQUENCE: 25

Ser Leu Trp Pro Arg Gly Trp Phe Ala Tyr
1               5                   10

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 8A12 VH CDR3

<400> SEQUENCE: 26
tcactttggc ccaggggctg gtttgcttac                                        30

<210> SEQ ID NO 27
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1E8 VL

<400> SEQUENCE: 27

Asp Ile Val Met Thr Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Glu Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Thr Phe Gly Gly Gly Thr Lys Leu Glu Ile Lys
            100                 105                 110

<210> SEQ ID NO 28
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 1E8 VL

<400> SEQUENCE: 28
gacattgtga tgacccagtc tccatcctcc ctagctgtgt cagttggaga gaaggttact      60
atgagctgca agtccagtca gagccttta tatagtagca atcaaaagaa ctacttggcc     120
tggtaccagc agaaaccagg gcagtctcct aaactgctga tttactgggc atccactagg     180
gaatctgggg tccctgatcg cttcacaggc agtggatctg ggacagaatt cactctcacc     240
atcagcagtg tgaaggctga agacctggca gtttattact gtcagcaata ttatagctat     300
ccgacgttcg gtggaggcac caagctggaa atcaaa                               336

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1E8 VH

<400> SEQUENCE: 29

Asp Val Lys Leu Gln Glu Ser Gly Pro Gly Leu Val Asn Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
            35                  40                  45

Met Gly Tyr Ile Ser Tyr Ser Gly Arg Thr Ser Tyr Lys Ser Ser Leu
 50                  55                  60

Lys Ser Arg Ile Ser Ile Thr Arg Asp Thr Ser Lys Asn Gln Phe Phe
 65                  70                  75                  80

Leu Glu Leu Asn Ser Val Thr Thr Glu Asp Thr Ala Thr Tyr Tyr Cys
                85                  90                  95

Ala Arg Asp Tyr Gly Asn Phe Val Gly Tyr Phe Asp Val Trp Gly Ala
            100                 105                 110

Gly Thr Thr Val Thr Val Ser Ser
            115                 120

<210> SEQ ID NO 30
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 1E8 VH

<400> SEQUENCE: 30
gatgtgaagc ttcaggagtc gggacctggc ctggtgaatc cttctcagtc tctgtccctc     60
acctgcactg tcactggcta ttcaatcacc agtgattatg cctggaactg gatccggcag    120
tttccaggaa acaaactgga gtggatgggc tacataagct acagtggtcg cactagctac    180
aaatcatctc tcaaaagtcg aatctctatc actcgagaca catccaagaa ccagttcttc    240
ctggagttga attctgtgac tactgaggac acagccacat attactgtgc aagagactat    300
ggtaacttcg taggttactt cgatgtctgg ggcgcaggga ccacggtcac cgtctcctca    360

<210> SEQ ID NO 31
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8A12 VL

<400> SEQUENCE: 31

Asp Ile Gln Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
             20                  25                  30

Leu Ser Trp Phe Gln Gln Lys Pro Gly Lys Ser Pro Lys Thr Leu Met
            35                  40                  45

Tyr Arg Ala Asn Arg Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys
            100                 105

```
<210> SEQ ID NO 32
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 8A12 VL

<400> SEQUENCE: 32
gacattctga tgacccagtc tccatcttcc atgtatgcat ctctaggaga gagagtcact      60
atcacttgca aggcgagtca ggacattaat agctatttaa gctggttcca gcagaaacca     120
gggaaatctc ctaagaccct gatgtatcgt gcaaacagat tggtagatgg ggtcccatca     180
aggttcagtg gcagtggatc tggccaagat tattctctca ccatcagcag cctggaatat     240
gaagatatgg gaatttatta ttgtctacag tatgatgagt ttcctcggac gttcggtgga     300
ggcaccaagc tggaaatcaa a                                                321

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8A12 VH

<400> SEQUENCE: 33

Asp Val Lys Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Glu
            20                  25                  30

Tyr Ala Trp Thr Trp Ile Arg Gln Phe Pro Gly Asn Lys Leu Glu Trp
        35                  40                  45

Met Gly Tyr Ile Asn Tyr Asn Gly Asn Thr Asn Leu Asn Pro Ser Leu
    50                  55                  60

Lys Ser Arg Ile Ser Ile Ile Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Leu Trp Pro Arg Gly Trp Phe Ala Tyr Trp Gly Gln Gly
            100                 105                 110

Thr Leu Val Thr Val Ser Ala
        115

<210> SEQ ID NO 34
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 8A12 VH

<400> SEQUENCE: 34
gatgtgaagc ttcaggagtc gggacctggc ctggtgaaac cttctcagtc tctgtccctc      60
acctgcactg tcactggcta ttcaatcacc agtgagtatg cctggacctg gatccggcag     120
tttccaggaa acaaactgga atggatgggc tacataaact acaatggcaa cactaactta     180
```

```
aatccatctc tcaaaagtcg aatctctatc attcgagaca catccaagaa ccagttcttc    240
ctgcagttga attctgtgac aactgaggac acagccacat attactgtgc aagatcactt    300
tggcccaggg gctggtttgc ttactggggc caagggactc tggtcactgt ctctgca      357
```

```
<210> SEQ ID NO 35
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1E8 light chain

<400> SEQUENCE: 35

Asp Ile Val Met Thr Gln Ser Pro Ser Ser Leu Ala Val Ser Val Gly
1               5                   10                  15

Glu Lys Val Thr Met Ser Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Glu Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Thr Phe Gly Gly Gly Thr Lys Leu Glu Ile Lys
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Arg Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

```
<210> SEQ ID NO 36
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1E8 Heavy chain

<400> SEQUENCE: 36

Asp Val Lys Leu Gln Glu Ser Gly Pro Gly Leu Val Asn Pro Ser Gln
1               5                   10                  15

Ser Leu Ser Leu Thr Cys Thr Val Thr Gly Tyr Ser Ile Thr Ser Asp
```

```
                 20                  25                  30
Tyr Ala Trp Asn Trp Ile Arg Gln Phe Pro Gly Asn Lys Leu Glu Trp
             35                  40                  45
Met Gly Tyr Ile Ser Tyr Ser Gly Arg Thr Ser Tyr Lys Ser Ser Leu
         50                  55                  60
Lys Ser Arg Ile Ser Ile Thr Arg Asp Thr Ser Lys Asn Gln Phe Phe
 65                  70                  75                  80
Leu Glu Leu Asn Ser Val Thr Thr Glu Asp Thr Ala Thr Tyr Tyr Cys
                 85                  90                  95
Ala Arg Asp Tyr Gly Asn Phe Val Gly Tyr Phe Asp Val Trp Gly Ala
             100                 105                 110
Gly Thr Thr Val Thr Val Ser Ser Ala Lys Thr Thr Ala Pro Ser Val
         115                 120                 125
Tyr Pro Leu Ala Pro Val Cys Gly Asp Thr Thr Gly Ser Ser Val Thr
         130                 135                 140
Leu Gly Cys Leu Val Lys Gly Tyr Phe Pro Glu Pro Val Thr Leu Thr
145                 150                 155                 160
Trp Asn Ser Gly Ser Leu Ser Ser Gly Val His Thr Phe Pro Ala Val
                 165                 170                 175
Leu Gln Ser Asp Leu Tyr Thr Leu Ser Ser Ser Val Thr Val Thr Ser
             180                 185                 190
Ser Thr Trp Pro Ser Gln Ser Ile Thr Cys Asn Val Ala His Pro Ala
         195                 200                 205
Ser Ser Thr Lys Val Asp Lys Lys Ile Glu Pro Arg Gly Pro Thr Ile
         210                 215                 220
Lys Pro Cys Pro Pro Cys Lys Cys Pro Ala Pro Asn Leu Leu Gly Gly
225                 230                 235                 240
Pro Ser Val Phe Ile Phe Pro Pro Lys Ile Lys Asp Val Leu Met Ile
                 245                 250                 255
Ser Leu Ser Pro Ile Val Thr Cys Val Val Val Asp Val Ser Glu Asp
             260                 265                 270
Asp Pro Asp Val Gln Ile Ser Trp Phe Val Asn Asn Val Glu Val His
         275                 280                 285
Thr Ala Gln Thr Gln Thr His Arg Glu Asp Tyr Asn Ser Thr Leu Arg
         290                 295                 300
Val Val Ser Ala Leu Pro Ile Gln His Gln Asp Trp Met Ser Gly Lys
305                 310                 315                 320
Glu Phe Lys Cys Lys Val Asn Asn Lys Asp Leu Pro Ala Pro Ile Glu
                 325                 330                 335
Arg Thr Ile Ser Lys Pro Lys Gly Ser Val Arg Ala Pro Gln Val Tyr
             340                 345                 350
Val Leu Pro Pro Pro Glu Glu Glu Met Thr Lys Lys Gln Val Thr Leu
         355                 360                 365
Thr Cys Met Val Thr Asp Phe Met Pro Glu Asp Ile Tyr Val Glu Trp
         370                 375                 380
Thr Asn Asn Gly Lys Thr Glu Leu Asn Tyr Lys Asn Thr Glu Pro Val
385                 390                 395                 400
Leu Asp Ser Asp Gly Ser Tyr Phe Met Tyr Ser Lys Leu Arg Val Glu
                 405                 410                 415
Lys Lys Asn Trp Val Glu Arg Asn Ser Tyr Ser Cys Ser Val Val His
             420                 425                 430
Glu Gly Leu His Asn His His Thr Thr Lys Ser Phe Ser Arg Thr Pro
         435                 440                 445
```

Gly Lys
    450

<210> SEQ ID NO 37
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8A12 light chain

<400> SEQUENCE: 37

Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Met
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Arg
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 38
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8A12 Heavy chain

<400> SEQUENCE: 38

Asp Val Lys Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Glu
            20                  25                  30

Tyr Ala Trp Thr Trp Ile Arg Gln Phe Pro Gly Asn Lys Leu Glu Trp

```
                35                  40                  45
Met Gly Tyr Ile Asn Tyr Asn Gly Asn Thr Asn Leu Asn Pro Ser Leu
            50                  55                  60

Lys Ser Arg Ile Ser Ile Ile Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                85                  90                  95

Ala Arg Ser Leu Trp Pro Arg Gly Trp Phe Ala Tyr Trp Gly Gln Gly
            100                 105                 110

Thr Leu Val Thr Val Ser Ala Ala Lys Thr Thr Ala Pro Ser Val Tyr
            115                 120                 125

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Asp Val Ser Glu Asp Asp
                260                 265                 270

Pro Asp Val Gln Ile Ser Trp Phe Val Asn Asn Val Glu Val His Thr
            275                 280                 285

Ala Gln Thr Gln Thr His Arg Glu Asp Tyr Asn Ser Thr Leu Arg Val
290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
            355                 360                 365

Cys Met Val Thr Asp Phe Met Pro Glu Asp Ile Tyr Val Glu Trp Thr
            370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val His Glu
            420                 425                 430

Gly Leu His Asn His His Thr Thr Lys Ser Phe Ser Arg Thr Pro Gly
            435                 440                 445

Lys
```

<210> SEQ ID NO 39
<211> LENGTH: 40
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: main binding site of Ab

<400> SEQUENCE: 39

Ala Gln Lys Ala Asp Lys Asn Glu Val Ala Ala Glu Val Ala Lys Leu
1               5                   10                  15

Leu Asp Leu Lys Lys Gln Leu Ala Val Ala Glu Gly Lys Pro Pro Glu
            20                  25                  30

Ala Pro Lys Gly Lys Lys Lys Lys
        35                  40

<210> SEQ ID NO 40
<211> LENGTH: 266
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: MRS fragment 1(1-256 aa)

<400> SEQUENCE: 40

Met Arg Leu Phe Val Ser Asp Gly Val Pro Gly Cys Leu Pro Val Leu
1               5                   10                  15

Ala Ala Ala Gly Arg Ala Arg Gly Arg Ala Glu Val Leu Ile Ser Thr
            20                  25                  30

Val Gly Pro Glu Asp Cys Val Val Pro Phe Leu Thr Arg Pro Lys Val
        35                  40                  45

Pro Val Leu Gln Leu Asp Ser Gly Asn Tyr Leu Phe Ser Thr Ser Ala
    50                  55                  60

Ile Cys Arg Tyr Phe Phe Leu Leu Ser Gly Trp Glu Gln Asp Asp Leu
65                  70                  75                  80

Thr Asn Gln Trp Leu Glu Trp Glu Ala Thr Glu Leu Gln Pro Ala Leu
                85                  90                  95

Ser Ala Ala Leu Tyr Tyr Leu Val Val Gln Gly Lys Lys Gly Glu Asp
            100                 105                 110

Val Leu Gly Ser Val Arg Arg Ala Leu Thr His Ile Asp His Ser Leu
        115                 120                 125

Ser Arg Gln Asn Cys Pro Phe Leu Ala Gly Glu Thr Glu Ser Leu Ala
    130                 135                 140

Asp Ile Val Leu Trp Gly Ala Leu Tyr Pro Leu Leu Gln Asp Pro Ala
145                 150                 155                 160

Tyr Leu Pro Glu Glu Leu Ser Ala Leu His Ser Trp Phe Gln Thr Leu
                165                 170                 175

Ser Thr Gln Glu Pro Cys Gln Arg Ala Ala Glu Thr Val Leu Lys Gln
            180                 185                 190

Gln Gly Val Leu Ala Leu Arg Pro Tyr Leu Gln Lys Gln Pro Gln Pro
        195                 200                 205

Ser Pro Ala Glu Gly Arg Ala Val Thr Asn Glu Pro Glu Glu Glu Glu
    210                 215                 220

Leu Ala Thr Leu Ser Glu Glu Ile Ala Met Ala Val Thr Ala Trp
225                 230                 235                 240

Glu Lys Gly Leu Glu Ser Leu Pro Pro Leu Arg Pro Gln Gln Asn Pro
            245                 250                 255

Val Leu Pro Val Ala Gly Glu Arg Asn Val
            260                 265

<210> SEQ ID NO 41
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MRS fragment 2(267-417 aa)

<400> SEQUENCE: 41

Leu Ile Thr Ser Ala Leu Pro Tyr Val Asn Asn Val Pro His Leu Gly
1               5                   10                  15

Asn Ile Ile Gly Cys Val Leu Ser Ala Asp Val Phe Ala Arg Tyr Ser
            20                  25                  30

Arg Leu Arg Gln Trp Asn Thr Leu Tyr Leu Cys Gly Thr Asp Glu Tyr
        35                  40                  45

Gly Thr Ala Thr Glu Thr Lys Ala Leu Glu Glu Gly Leu Thr Pro Gln
    50                  55                  60

Glu Ile Cys Asp Lys Tyr His Ile Ile His Ala Asp Ile Tyr Arg Trp
65                  70                  75                  80

Phe Asn Ile Ser Phe Asp Ile Phe Gly Arg Thr Thr Thr Pro Gln Gln
                85                  90                  95

Thr Lys Ile Thr Gln Asp Ile Phe Gln Gln Leu Leu Lys Arg Gly Phe
            100                 105                 110

Val Leu Gln Asp Thr Val Glu Gln Leu Arg Cys Glu His Cys Ala Arg
        115                 120                 125

Phe Leu Ala Asp Arg Phe Val Glu Gly Val Cys Pro Phe Cys Gly Tyr
    130                 135                 140

Glu Glu Ala Arg Gly Asp Gln
145                 150

<210> SEQ ID NO 42
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MRS fragment 3(267-597 aa)

<400> SEQUENCE: 42

Leu Ile Thr Ser Ala Leu Pro Tyr Val Asn Asn Val Pro His Leu Gly
1               5                   10                  15

Asn Ile Ile Gly Cys Val Leu Ser Ala Asp Val Phe Ala Arg Tyr Ser
            20                  25                  30

Arg Leu Arg Gln Trp Asn Thr Leu Tyr Leu Cys Gly Thr Asp Glu Tyr
        35                  40                  45

Gly Thr Ala Thr Glu Thr Lys Ala Leu Glu Glu Gly Leu Thr Pro Gln
    50                  55                  60

Glu Ile Cys Asp Lys Tyr His Ile Ile His Ala Asp Ile Tyr Arg Trp
65                  70                  75                  80

Phe Asn Ile Ser Phe Asp Ile Phe Gly Arg Thr Thr Thr Pro Gln Gln

```
                85                  90                  95
Thr Lys Ile Thr Gln Asp Ile Phe Gln Gln Leu Leu Lys Arg Gly Phe
                100                 105                 110

Val Leu Gln Asp Thr Val Glu Gln Leu Arg Cys Glu His Cys Ala Arg
                115                 120                 125

Phe Leu Ala Asp Arg Phe Val Glu Gly Val Cys Pro Phe Cys Gly Tyr
        130                 135                 140

Glu Glu Ala Arg Gly Asp Gln Cys Asp Lys Cys Gly Lys Leu Ile Asn
145                 150                 155                 160

Ala Val Glu Leu Lys Lys Pro Gln Cys Lys Val Cys Arg Ser Cys Pro
                165                 170                 175

Val Val Gln Ser Ser Gln His Leu Phe Leu Asp Leu Pro Lys Leu Glu
                180                 185                 190

Lys Arg Leu Glu Glu Trp Leu Gly Arg Thr Leu Pro Gly Ser Asp Trp
            195                 200                 205

Thr Pro Asn Ala Gln Phe Ile Thr Arg Ser Trp Leu Arg Asp Gly Leu
        210                 215                 220

Lys Pro Arg Cys Ile Thr Arg Asp Leu Lys Trp Gly Thr Pro Val Pro
225                 230                 235                 240

Leu Glu Gly Phe Glu Asp Lys Val Phe Tyr Val Trp Phe Asp Ala Thr
                245                 250                 255

Ile Gly Tyr Leu Ser Ile Thr Ala Asn Tyr Thr Asp Gln Trp Glu Arg
                260                 265                 270

Trp Trp Lys Asn Pro Glu Gln Val Asp Leu Tyr Gln Phe Met Ala Lys
            275                 280                 285

Asp Asn Val Pro Phe His Ser Leu Val Phe Pro Cys Ser Ala Leu Gly
        290                 295                 300

Ala Glu Asp Asn Tyr Thr Leu Val Ser His Leu Ile Ala Thr Glu Tyr
305                 310                 315                 320

Leu Asn Tyr Glu Asp Gly Lys Phe Ser Lys Ser
                325                 330

<210> SEQ ID NO 43
<211> LENGTH: 597
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MRS fragment 4(1-597 aa)

<400> SEQUENCE: 43

Met Arg Leu Phe Val Ser Asp Gly Val Pro Gly Cys Leu Pro Val Leu
1               5                   10                  15

Ala Ala Ala Gly Arg Ala Arg Gly Arg Ala Glu Val Leu Ile Ser Thr
                20                  25                  30

Val Gly Pro Glu Asp Cys Val Val Pro Phe Leu Thr Arg Pro Lys Val
            35                  40                  45

Pro Val Leu Gln Leu Asp Ser Gly Asn Tyr Leu Phe Ser Thr Ser Ala
        50                  55                  60

Ile Cys Arg Tyr Phe Phe Leu Leu Ser Gly Trp Glu Gln Asp Asp Leu
65                  70                  75                  80

Thr Asn Gln Trp Leu Glu Trp Glu Ala Thr Glu Leu Gln Pro Ala Leu
                85                  90                  95

Ser Ala Ala Leu Tyr Tyr Leu Val Val Gln Gly Lys Lys Gly Glu Asp
```

```
            100                 105                 110
Val Leu Gly Ser Val Arg Arg Ala Leu Thr His Ile Asp His Ser Leu
            115                 120                 125

Ser Arg Gln Asn Cys Pro Phe Leu Ala Gly Glu Thr Glu Ser Leu Ala
            130                 135                 140

Asp Ile Val Leu Trp Gly Ala Leu Tyr Pro Leu Leu Gln Asp Pro Ala
145                 150                 155                 160

Tyr Leu Pro Glu Glu Leu Ser Ala Leu His Ser Trp Phe Gln Thr Leu
            165                 170                 175

Ser Thr Gln Glu Pro Cys Gln Arg Ala Ala Glu Thr Val Leu Lys Gln
            180                 185                 190

Gln Gly Val Leu Ala Leu Arg Pro Tyr Leu Gln Lys Gln Pro Gln Pro
            195                 200                 205

Ser Pro Ala Glu Gly Arg Ala Val Thr Asn Glu Pro Glu Glu Glu Glu
            210                 215                 220

Leu Ala Thr Leu Ser Glu Glu Ile Ala Met Ala Val Thr Ala Trp
225                 230                 235                 240

Glu Lys Gly Leu Glu Ser Leu Pro Pro Leu Arg Pro Gln Gln Asn Pro
            245                 250                 255

Val Leu Pro Val Ala Gly Glu Arg Asn Val Leu Ile Thr Ser Ala Leu
            260                 265                 270

Pro Tyr Val Asn Asn Val Pro His Leu Gly Asn Ile Ile Gly Cys Val
            275                 280                 285

Leu Ser Ala Asp Val Phe Ala Arg Tyr Ser Arg Leu Arg Gln Trp Asn
            290                 295                 300

Thr Leu Tyr Leu Cys Gly Thr Asp Glu Tyr Gly Thr Ala Thr Glu Thr
305                 310                 315                 320

Lys Ala Leu Glu Glu Gly Leu Thr Pro Gln Glu Ile Cys Asp Lys Tyr
            325                 330                 335

His Ile Ile His Ala Asp Ile Tyr Arg Trp Phe Asn Ile Ser Phe Asp
            340                 345                 350

Ile Phe Gly Arg Thr Thr Thr Pro Gln Gln Thr Lys Ile Thr Gln Asp
            355                 360                 365

Ile Phe Gln Gln Leu Leu Lys Arg Gly Phe Val Leu Gln Asp Thr Val
            370                 375                 380

Glu Gln Leu Arg Cys Glu His Cys Ala Arg Phe Leu Ala Asp Arg Phe
385                 390                 395                 400

Val Glu Gly Val Cys Pro Phe Cys Gly Tyr Glu Glu Ala Arg Gly Asp
            405                 410                 415

Gln Cys Asp Lys Cys Gly Lys Leu Ile Asn Ala Val Glu Leu Lys Lys
            420                 425                 430

Pro Gln Cys Lys Val Cys Arg Ser Cys Pro Val Val Gln Ser Ser Gln
            435                 440                 445

His Leu Phe Leu Asp Leu Pro Lys Leu Glu Lys Arg Leu Glu Glu Trp
            450                 455                 460

Leu Gly Arg Thr Leu Pro Gly Ser Asp Trp Thr Pro Asn Ala Gln Phe
465                 470                 475                 480

Ile Thr Arg Ser Trp Leu Arg Asp Gly Leu Lys Pro Arg Cys Ile Thr
            485                 490                 495

Arg Asp Leu Lys Trp Gly Thr Pro Val Pro Leu Glu Gly Phe Glu Asp
            500                 505                 510

Lys Val Phe Tyr Val Trp Phe Asp Ala Thr Ile Gly Tyr Leu Ser Ile
            515                 520                 525
```

```
Thr Ala Asn Tyr Thr Asp Gln Trp Glu Arg Trp Trp Lys Asn Pro Glu
    530                 535                 540

Gln Val Asp Leu Tyr Gln Phe Met Ala Lys Asp Asn Val Pro Phe His
545                 550                 555                 560

Ser Leu Val Phe Pro Cys Ser Ala Leu Gly Ala Glu Asp Asn Tyr Thr
                565                 570                 575

Leu Val Ser His Leu Ile Ala Thr Glu Tyr Leu Asn Tyr Glu Asp Gly
            580                 585                 590

Lys Phe Ser Lys Ser
            595

<210> SEQ ID NO 44
<211> LENGTH: 303
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MRS fragment 5(598-900 aa)

<400> SEQUENCE: 44

Arg Gly Val Gly Val Phe Gly Asp Met Ala Gln Asp Thr Gly Ile Pro
1               5                   10                  15

Ala Asp Ile Trp Arg Phe Tyr Leu Leu Tyr Ile Arg Pro Glu Gly Gln
            20                  25                  30

Asp Ser Ala Phe Ser Trp Thr Asp Leu Leu Leu Lys Asn Asn Ser Glu
        35                  40                  45

Leu Leu Asn Asn Leu Gly Asn Phe Ile Asn Arg Ala Gly Met Phe Val
50                  55                  60

Ser Lys Phe Phe Gly Gly Tyr Val Pro Glu Met Val Leu Thr Pro Asp
65                  70                  75                  80

Asp Gln Arg Leu Leu Ala His Val Thr Leu Glu Leu Gln His Tyr His
                85                  90                  95

Gln Leu Leu Glu Lys Val Arg Ile Arg Asp Ala Leu Arg Ser Ile Leu
            100                 105                 110

Thr Ile Ser Arg His Gly Asn Gln Tyr Ile Gln Val Asn Glu Pro Trp
        115                 120                 125

Lys Arg Ile Lys Gly Ser Glu Ala Asp Arg Gln Arg Ala Gly Thr Val
130                 135                 140

Thr Gly Leu Ala Val Asn Ile Ala Ala Leu Leu Ser Val Met Leu Gln
145                 150                 155                 160

Pro Tyr Met Pro Thr Val Ser Ala Thr Ile Gln Ala Gln Leu Gln Leu
                165                 170                 175

Pro Pro Pro Ala Cys Ser Ile Leu Leu Thr Asn Phe Leu Cys Thr Leu
            180                 185                 190

Pro Ala Gly His Gln Ile Gly Thr Val Ser Pro Leu Phe Gln Lys Leu
        195                 200                 205

Glu Asn Asp Gln Ile Glu Ser Leu Arg Gln Arg Phe Gly Gly Gly Gln
    210                 215                 220

Ala Lys Thr Ser Pro Lys Pro Ala Val Val Glu Thr Val Thr Thr Ala
225                 230                 235                 240

Lys Pro Gln Gln Ile Gln Ala Leu Met Asp Glu Val Thr Lys Gln Gly
                245                 250                 255

Asn Ile Val Arg Glu Leu Lys Ala Gln Lys Ala Asp Lys Asn Glu Val
            260                 265                 270
```

Ala Ala Glu Val Ala Lys Leu Leu Asp Leu Lys Lys Gln Leu Ala Val
        275                 280                 285

Ala Glu Gly Lys Pro Pro Glu Ala Pro Lys Gly Lys Lys Lys
    290                 295                 300

<210> SEQ ID NO 45
<211> LENGTH: 603
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MRS fragment 6(298-900 aa)

<400> SEQUENCE: 45

Ser Arg Leu Arg Gln Trp Asn Thr Leu Tyr Leu Cys Gly Thr Asp Glu
1               5                   10                  15

Tyr Gly Thr Ala Thr Glu Thr Lys Ala Leu Glu Glu Gly Leu Thr Pro
            20                  25                  30

Gln Glu Ile Cys Asp Lys Tyr His Ile Ile His Ala Asp Ile Tyr Arg
        35                  40                  45

Trp Phe Asn Ile Ser Phe Asp Ile Phe Gly Arg Thr Thr Thr Pro Gln
    50                  55                  60

Gln Thr Lys Ile Thr Gln Asp Ile Phe Gln Gln Leu Leu Lys Arg Gly
65                  70                  75                  80

Phe Val Leu Gln Asp Thr Val Glu Gln Leu Arg Cys Glu His Cys Ala
                85                  90                  95

Arg Phe Leu Ala Asp Arg Phe Val Glu Gly Val Cys Pro Phe Cys Gly
            100                 105                 110

Tyr Glu Glu Ala Arg Gly Asp Gln Cys Asp Lys Cys Gly Lys Leu Ile
        115                 120                 125

Asn Ala Val Glu Leu Lys Lys Pro Gln Cys Lys Val Cys Arg Ser Cys
    130                 135                 140

Pro Val Val Gln Ser Ser Gln His Leu Phe Leu Asp Leu Pro Lys Leu
145                 150                 155                 160

Glu Lys Arg Leu Glu Glu Trp Leu Gly Arg Thr Leu Pro Gly Ser Asp
                165                 170                 175

Trp Thr Pro Asn Ala Gln Phe Ile Thr Arg Ser Trp Leu Arg Asp Gly
            180                 185                 190

Leu Lys Pro Arg Cys Ile Thr Arg Asp Leu Lys Trp Gly Thr Pro Val
        195                 200                 205

Pro Leu Glu Gly Phe Glu Asp Lys Val Phe Tyr Val Trp Phe Asp Ala
    210                 215                 220

Thr Ile Gly Tyr Leu Ser Ile Thr Ala Asn Tyr Thr Asp Gln Trp Glu
225                 230                 235                 240

Arg Trp Trp Lys Asn Pro Glu Gln Val Asp Leu Tyr Gln Phe Met Ala
                245                 250                 255

Lys Asp Asn Val Pro Phe His Ser Leu Val Phe Pro Cys Ser Ala Leu
            260                 265                 270

Gly Ala Glu Asp Asn Tyr Thr Leu Val Ser His Leu Ile Ala Thr Glu
        275                 280                 285

Tyr Leu Asn Tyr Glu Asp Gly Lys Phe Ser Lys Ser Arg Gly Val Gly
    290                 295                 300

Val Phe Gly Asp Met Ala Gln Asp Thr Gly Ile Pro Ala Asp Ile Trp
305                 310                 315                 320

```
Arg Phe Tyr Leu Leu Tyr Ile Arg Pro Glu Gly Gln Asp Ser Ala Phe
                325                 330                 335

Ser Trp Thr Asp Leu Leu Lys Asn Asn Ser Glu Leu Leu Asn Asn
        340                 345                 350

Leu Gly Asn Phe Ile Asn Arg Ala Gly Met Phe Val Ser Lys Phe Phe
            355                 360                 365

Gly Gly Tyr Val Pro Glu Met Val Leu Thr Pro Asp Asp Gln Arg Leu
        370                 375                 380

Leu Ala His Val Thr Leu Glu Leu Gln His Tyr His Gln Leu Leu Glu
385                 390                 395                 400

Lys Val Arg Ile Arg Asp Ala Leu Arg Ser Ile Leu Thr Ile Ser Arg
                405                 410                 415

His Gly Asn Gln Tyr Ile Gln Val Asn Glu Pro Trp Lys Arg Ile Lys
            420                 425                 430

Gly Ser Glu Ala Asp Arg Gln Arg Ala Gly Thr Val Thr Gly Leu Ala
        435                 440                 445

Val Asn Ile Ala Ala Leu Leu Ser Val Met Leu Gln Pro Tyr Met Pro
    450                 455                 460

Thr Val Ser Ala Thr Ile Gln Ala Gln Leu Gln Leu Pro Pro Pro Ala
465                 470                 475                 480

Cys Ser Ile Leu Leu Thr Asn Phe Leu Cys Thr Leu Pro Ala Gly His
                485                 490                 495

Gln Ile Gly Thr Val Ser Pro Leu Phe Gln Lys Leu Glu Asn Asp Gln
            500                 505                 510

Ile Glu Ser Leu Arg Gln Arg Phe Gly Gly Gln Ala Lys Thr Ser
        515                 520                 525

Pro Lys Pro Ala Val Val Glu Thr Val Thr Thr Ala Lys Pro Gln Gln
    530                 535                 540

Ile Gln Ala Leu Met Asp Glu Val Thr Lys Gln Gly Asn Ile Val Arg
545                 550                 555                 560

Glu Leu Lys Ala Gln Lys Ala Asp Lys Asn Glu Val Ala Ala Glu Val
                565                 570                 575

Ala Lys Leu Leu Asp Leu Lys Lys Gln Leu Ala Val Ala Glu Gly Lys
            580                 585                 590

Pro Pro Glu Ala Pro Lys Gly Lys Lys Lys Lys
        595                 600

<210> SEQ ID NO 46
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MRS fragment 7(660-860 aa)

<400> SEQUENCE: 46

Phe Val Ser Lys Phe Phe Gly Gly Tyr Val Pro Glu Met Val Leu Thr
1               5                   10                  15

Pro Asp Asp Gln Arg Leu Leu Ala His Val Thr Leu Glu Leu Gln His
            20                  25                  30

Tyr His Gln Leu Leu Glu Lys Val Arg Ile Arg Asp Ala Leu Arg Ser
        35                  40                  45

Ile Leu Thr Ile Ser Arg His Gly Asn Gln Tyr Ile Gln Val Asn Glu
    50                  55                  60
```

Pro Trp Lys Arg Ile Lys Gly Ser Glu Ala Asp Arg Gln Arg Ala Gly
65                  70                  75                  80

Thr Val Thr Gly Leu Ala Val Asn Ile Ala Ala Leu Leu Ser Val Met
            85                  90                  95

Leu Gln Pro Tyr Met Pro Thr Val Ser Ala Thr Ile Gln Ala Gln Leu
            100                 105                 110

Gln Leu Pro Pro Pro Ala Cys Ser Ile Leu Leu Thr Asn Phe Leu Cys
            115                 120                 125

Thr Leu Pro Ala Gly His Gln Ile Gly Thr Val Ser Pro Leu Phe Gln
130                 135                 140

Lys Leu Glu Asn Asp Gln Ile Glu Ser Leu Arg Gln Arg Phe Gly Gly
145                 150                 155                 160

Gly Gln Ala Lys Thr Ser Pro Lys Pro Ala Val Val Glu Thr Val Thr
                165                 170                 175

Thr Ala Lys Pro Gln Gln Ile Gln Ala Leu Met Asp Glu Val Thr Lys
            180                 185                 190

Gln Gly Asn Ile Val Arg Glu Leu Lys
            195                 200

<210> SEQ ID NO 47
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MRS fragment 8(660-900 aa)

<400> SEQUENCE: 47

Phe Val Ser Lys Phe Gly Gly Tyr Val Pro Glu Met Val Leu Thr
1               5                   10                  15

Pro Asp Asp Gln Arg Leu Leu Ala His Val Thr Leu Glu Leu Gln His
            20                  25                  30

Tyr His Gln Leu Leu Glu Lys Val Arg Ile Arg Asp Ala Leu Arg Ser
            35                  40                  45

Ile Leu Thr Ile Ser Arg His Gly Asn Gln Tyr Ile Gln Val Asn Glu
50                  55                  60

Pro Trp Lys Arg Ile Lys Gly Ser Glu Ala Asp Arg Gln Arg Ala Gly
65                  70                  75                  80

Thr Val Thr Gly Leu Ala Val Asn Ile Ala Ala Leu Leu Ser Val Met
            85                  90                  95

Leu Gln Pro Tyr Met Pro Thr Val Ser Ala Thr Ile Gln Ala Gln Leu
            100                 105                 110

Gln Leu Pro Pro Pro Ala Cys Ser Ile Leu Leu Thr Asn Phe Leu Cys
            115                 120                 125

Thr Leu Pro Ala Gly His Gln Ile Gly Thr Val Ser Pro Leu Phe Gln
130                 135                 140

Lys Leu Glu Asn Asp Gln Ile Glu Ser Leu Arg Gln Arg Phe Gly Gly
145                 150                 155                 160

Gly Gln Ala Lys Thr Ser Pro Lys Pro Ala Val Val Glu Thr Val Thr
                165                 170                 175

Thr Ala Lys Pro Gln Gln Ile Gln Ala Leu Met Asp Glu Val Thr Lys
            180                 185                 190

Gln Gly Asn Ile Val Arg Glu Leu Lys Ala Gln Lys Ala Asp Lys Asn
            195                 200                 205

```
Glu Val Ala Ala Glu Val Ala Lys Leu Leu Asp Leu Lys Lys Gln Leu
    210                 215                 220
Ala Val Ala Glu Gly Lys Pro Pro Glu Ala Pro Lys Gly Lys Lys Lys
225                 230                 235                 240
Lys
```

```
<210> SEQ ID NO 48
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: MRS fragment 9(730-900 aa)

<400> SEQUENCE: 48

Gly Ser Glu Ala Asp Arg Gln Arg Ala Gly Thr Val Thr Gly Leu Ala
1               5                   10                  15

Val Asn Ile Ala Ala Leu Leu Ser Val Met Leu Gln Pro Tyr Met Pro
                20                  25                  30

Thr Val Ser Ala Thr Ile Gln Ala Gln Leu Gln Leu Pro Pro Pro Ala
            35                  40                  45

Cys Ser Ile Leu Leu Thr Asn Phe Leu Cys Thr Leu Pro Ala Gly His
    50                  55                  60

Gln Ile Gly Thr Val Ser Pro Leu Phe Gln Lys Leu Glu Asn Asp Gln
65                  70                  75                  80

Ile Glu Ser Leu Arg Gln Arg Phe Gly Gly Gln Ala Lys Thr Ser
                85                  90                  95

Pro Lys Pro Ala Val Val Glu Thr Val Thr Thr Ala Lys Pro Gln Gln
            100                 105                 110

Ile Gln Ala Leu Met Asp Glu Val Thr Lys Gln Gly Asn Ile Val Arg
        115                 120                 125

Glu Leu Lys Ala Gln Lys Ala Asp Lys Asn Glu Val Ala Ala Glu Val
    130                 135                 140

Ala Lys Leu Leu Asp Leu Lys Lys Gln Leu Ala Val Ala Glu Gly Lys
145                 150                 155                 160

Pro Pro Glu Ala Pro Lys Gly Lys Lys Lys
                165                 170
```

```
<210> SEQ ID NO 49
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Homo sapiens AIMP3 protein

<400> SEQUENCE: 49

Met Ala Ala Ala Ala Glu Leu Ser Leu Leu Glu Lys Ser Leu Gly Leu
1               5                   10                  15

Ser Lys Gly Asn Lys Tyr Ser Ala Gln Gly Glu Arg Gln Ile Pro Val
                20                  25                  30

Leu Gln Thr Asn Asn Gly Pro Ser Leu Thr Gly Leu Thr Thr Ile Ala
            35                  40                  45

Ala His Leu Val Lys Gln Ala Asn Lys Glu Tyr Leu Leu Gly Ser Thr
    50                  55                  60
```

```
Ala Glu Glu Lys Ala Ile Val Gln Gln Trp Leu Glu Tyr Arg Val Thr
 65              70                  75                  80

Gln Val Asp Gly His Ser Ser Lys Asn Asp Ile His Thr Leu Leu Lys
             85                  90                  95

Asp Leu Asn Ser Tyr Leu Glu Asp Lys Val Tyr Leu Thr Gly Tyr Asn
            100                 105                 110

Phe Thr Leu Ala Asp Ile Leu Leu Tyr Tyr Gly Leu His Arg Phe Ile
        115                 120                 125

Val Asp Leu Thr Val Gln Glu Lys Glu Lys Tyr Leu Asn Val Ser Arg
        130             135                 140

Trp Phe Cys His Ile Gln His Tyr Pro Gly Ile Arg Gln His Leu Ser
145             150                 155                 160

Ser Val Val Phe Ile Lys Asn Arg Leu Tyr Thr Asn Ser His
                165                 170
```